US012569506B2

(12) United States Patent
Lane et al.

(10) Patent No.: US 12,569,506 B2
(45) Date of Patent: Mar. 10, 2026

(54) METHODS OF TREATING OSTEONECROSIS WITH LLP2A-BISPHOSPHONATE COMPOUNDS

(71) Applicant: The Regents of the University of California, Oakland, CA (US)

(72) Inventors: Nancy Lane, Hillsborough, CA (US); Wei Yao, El Dorado Hills, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/996,401

(22) Filed: Aug. 18, 2020

(65) Prior Publication Data

US 2021/0205338 A1 Jul. 8, 2021

Related U.S. Application Data

(63) Continuation of application No. 16/034,890, filed on Jul. 13, 2018, now abandoned, which is a continuation of application No. PCT/US2017/013482, filed on Jan. 13, 2017.

(60) Provisional application No. 62/278,921, filed on Jan. 14, 2016.

(51) Int. Cl.

| | |
|---|---|
| ***A61K 31/663*** | (2006.01) |
| ***A61K 9/00*** | (2006.01) |
| ***A61K 35/28*** | (2015.01) |
| ***A61K 35/64*** | (2015.01) |
| ***A61K 47/54*** | (2017.01) |
| ***A61K 47/64*** | (2017.01) |
| ***A61P 19/08*** | (2006.01) |
| ***A61P 19/10*** | (2006.01) |
| ***C07K 5/09*** | (2006.01) |

(52) U.S. Cl.

CPC .......... *A61K 31/663* (2013.01); *A61K 9/0019* (2013.01); *A61K 35/28* (2013.01); *A61K 35/64* (2013.01); *A61K 47/545* (2017.08); *A61K 47/548* (2017.08); *A61K 47/64* (2017.08); *A61P 19/10* (2018.01); *C07K 5/0815* (2013.01)

(58) Field of Classification Search

CPC .. A61K 31/663; A61K 47/548; A61K 47/545; A61K 47/64; A61K 9/0019; A61P 19/08; A61P 19/10

See application file for complete search history.

(56) References Cited

U.S. PATENT DOCUMENTS

| | | | |
|---|---|---|---|
| 9,119,884 B2 | 9/2015 | Lam et al. | |
| 9,561,256 B2 | 2/2017 | Lam et al. | |
| 10,494,401 B2 | 12/2019 | Lam et al. | |
| 2009/0005347 A1 | 1/2009 | Little et al. | |
| 2014/0056855 A1 | 2/2014 | Lam et al. | |
| 2016/0243250 A1 | 8/2016 | Lane et al. | |
| 2017/0174722 A1 | 6/2017 | Lam et al. | |
| 2021/0261612 A1* | 8/2021 | Lam | C07K 5/0821 |

FOREIGN PATENT DOCUMENTS

| | | |
|---|---|---|
| WO | 2012/031228 A2 | 3/2012 |
| WO | 2013/032527 A1 | 3/2013 |
| WO | 2015/051327 A1 | 4/2015 |
| WO | 2017/123977 A1 | 7/2017 |

OTHER PUBLICATIONS

Assouline-Dayan et al. Seminars in Arthritis and Rheumatism 2002, 32 (2), 94-124.*
Karim et al. Ann Transl Med 2015, 3(1), 6, pp. 1-11.*
Martin J Bone Metab 2014, 21, 8-20.*
Extended European Search Report mailed on Aug. 5, 2019 for EP Application No. 17739064.8, 9 pages.
Lane et al., "A Bone-Seeking Anabolic Agent, LLP2A-Ale, Prevented and Restored Glucocorticoid-Induced Bone Loss", Journal of Bone and Mineral Research, vol. 30, Abstract, Database Accession No. EMB-620769202, Elsevier Science Publishers, Feb. 1, 2015, 2 pages.
Lay et al., "Effect of LLP 2A-Ale on Fracture Healing in Growing Mice", Journal of Bone and Mineral Research, vol. 30, Conference Abstract, Database Accession No. EMB-620768872, Elsevier Science Publishers, Feb. 1, 2015, 1 page.
Lin, J.H., "Bisphosphonates: A Review of Their Pharmacokinetic Properties", Bone, vol. 18, No. 2 Feb. 1996, pp. 75-85.
Yao et al., "Targeted Delivery of Mesenchymal Stem Cells to the Bone", Bone, vol. 70, 2015, pp. 62-65.
Nishii et al., "Bisphosphonate Treatment in Osteonecrosis of the Femoral Head", Nihon Rinsho, Nov. 28, 2007, vol. 65, Suppl. 9, pp. 537-541.
Silverman, "Bisphosphonate use in conditions other than osteoporosis" Ann. N. Y. Acad. Sci., 1218(2011), pp. 33-37.
Pisuitthanakan et al. "Intravenous Bisphosphonate Therapy for Children Who Have a Traumatic Fracture Neck of Femur and Osteonecrosis: A Case Report", J Med Assoc Thai, 2012, vol. 95, No. 2, pp. 275-278.
Jureus et al., "Treatment of Spontaneous Osteonecrosis of the Knee (Sponk) by a Bisphosphonate", Acta Orthopaedica, vol. 83, No. 5, 2012, pp. 511-514.
"ASBMR 2015 Annual Meeting" Journal of Bone and Mineral Research, 2015, vol. 30, No. Supplemental, pp. S143, SA0150.
"Diagnosis and Treatment of Osteoarthrosis", Li Xingyong, p. 126, Tianjin Science and Technology Press, 2011, 2 pages.
Shangli, et al. "Basic and Clinical of Osteonecrosis", People's Military Doctor Press, 2008, 9 pages.

(Continued)

*Primary Examiner* — Irina Neagu
(74) *Attorney, Agent, or Firm* — Kilpatrick Townsend & Stockton LLP

(57) ABSTRACT

Methods of treating osteonecrosis in a subject are provided. In some embodiments, the method comprises administering to a subject having or suspected of having osteonecrosis a pharmaceutical composition comprising a conjugate of an LLP2A peptidomimetic ligand and a bisphosphonate drug. In some embodiments, the pharmaceutical composition comprises a conjugate of LLP2A and alendronate (LLP2A-Ale). In some embodiments, the method further comprises administering exogenous mesenchymal stem cells.

13 Claims, 17 Drawing Sheets

(56) References Cited

OTHER PUBLICATIONS

Tanaka, Y. et.al., "Mesenchymal stem cells for the treatment and repair of inflammatory arthritis," *Japanese Journal of Clinical Immunology,* 2015, vol. 38, Issue 2, pp. 86-92.
Kikuiri, T., "Role of Immune Cells in Development of Bisphosphonate-Related Osteonecrosis of the Jaw," *Pediatric Dental Journal* (written in Japanese), 2015, vol. 53, Issue 1, pp. 1-8.
Azuma, N. et.al., "II. To avoid missing complications, 2. Osteoporosis," *Internal Medicine* (written in Japanese), 2009, vol. 98, Issue 10, pp. 2460-2467.

* cited by examiner

METHODS OF TREATING OSTEONECROSIS WITH LLP2A-BISPHOSPHONATE COMPOUNDS

CROSS-REFERENCE TO RELATED APPLICATIONS

The present application is a continuation of U.S. application Ser. No. 16/034,890, filed Jul. 13, 2018, which is a continuation of International Patent Application No. PCT/US2017/013482, filed Jan. 13, 2017, which claims priority to U.S. Provisional Application No. 62/278,921, filed Jan. 14, 2016, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. AR061366, awarded by the National Institutes of Health. The Government has certain rights in this invention.

BACKGROUND OF THE INVENTION

Osteonecrosis, also known as avascular necrosis, is a disorder in which impaired blood supply in a region of bone leads to the death of the bone in that region. There are two types of osteonecrosis, traumatic osteonecrosis and non-traumatic osteonecrosis. In traumatic osteonecrosis, an injury to a bone, such as a fracture or a dislocation, damages the blood vessels in the bone. In nontraumatic osteonecrosis, the impairment of blood supply and bone death occurs without direct trauma or injury. In some cases, the cause of osteonecrosis in a patient is unknown (idiopathic osteonecrosis).

Osteonecrosis can affect any of a number of bones and joints in the body, including but not limited to the hip, shoulder, knee, ankle, wrist, and jaw. If left untreated, or if early treatment is not successful, osteonecrosis can result in the collapse of bones and destruction of joints surrounding bones.

BRIEF SUMMARY OF THE INVENTION

In one aspect, methods of treating osteonecrosis in a subject are provided. In some embodiments, the method comprises:

administering to the subject a pharmaceutical composition comprising a conjugate of an LLP2A peptidomimetic ligand and a bisphosphonate drug.

In some embodiments, the subject has or is suspected of having osteonecrosis in at least one bone, e.g., a femur, hip, knee, shoulder, ankle, wrist, or jaw bone. In some embodiments, prior to the administering step, the method further comprises identifying a subject having at least one osteonecrotic lesion in at least one bone. In some embodiments, the method further comprises measuring the size of the at least one osteonecrotic lesion prior to the step of administering the pharmaceutical composition. In some embodiments, the method further comprises, subsequent to the step of administering the pharmaceutical composition, measuring the size of the at least one osteonecrotic lesion and detecting a decrease in the size of the osteonecrotic lesion relative to the size of the osteonecrotic lesion prior to the administering step. In some embodiments, a decrease in the size of the osteonecrotic lesion, relative to the size of the osteonecrotic lesion prior to the step of administering the pharmaceutical composition, is indicative that the osteonecrosis is being treated in the subject.

In another aspect, methods of increasing vascular density in an osteonecrotic tissue (e.g., in a subject, e.g., a subject having or suspected of having an osteonecrotic tissue) are provided. In some embodiments, the method comprises:

administering to the subject a pharmaceutical composition comprising a conjugate of an LLP2A peptidomimetic ligand and a bisphosphonate drug.

In some embodiments, prior to the administering step, the method further comprises identifying a subject having an osteonecrotic tissue (e.g., at least one osteonecrotic lesion in at least one bone). In some embodiments, the method further comprises measuring the amount of vascular density in the at least one bone having at least one osteonecrotic lesion (e.g., measuring the amount of vascular density in or around the area of the osteonecrotic lesion) prior to the step of administering the pharmaceutical composition. In some embodiments, the method further comprises measuring the amount of vascular density in the at least one bone having at least one osteonecrotic lesion (e.g., measuring the amount of vascular density in or around the area of the osteonecrotic lesion) subsequent to the step of administering the pharmaceutical composition. In some embodiments, a higher amount of vascular density (e.g., in or around the area of the osteonecrotic lesion), relative to the amount of vascular density prior to the step of administering the pharmaceutical composition, is indicative that the vascular density is being increased in the osteonecrotic tissue.

In yet another aspect, methods of preventing or reducing cell death in an osteonecrotic tissue (e.g., in a subject, a subject having or suspected of having an osteonecrotic tissue) are provided. In some embodiments, the method comprises:

administering to the subject a pharmaceutical composition comprising a conjugate of an LLP2A peptidomimetic ligand and a bisphosphonate drug.

In some embodiments, prior to the administering step, the method further comprises identifying a subject having an osteonecrotic tissue (e.g., at least one osteonecrotic lesion in at least one bone). In some embodiments, the method further comprises measuring the amount of apoptotic and/or necrotic cells in the at least one osteonecrotic tissue (e.g., in or around the area of the at least one osteonecrotic lesion) prior to the step of administering the pharmaceutical composition. In some embodiments, the method further comprises measuring the amount of apoptotic and/or necrotic cells in the at least one osteonecrotic tissue (e.g., in or around the area of the at least one osteonecrotic lesion) subsequent to the step of administering the pharmaceutical composition. In some embodiments, a decrease in the amount of apoptotic and/or necrotic cells in the at least one osteonecrotic tissue (e.g., in or around the area of the at least one osteonecrotic lesion), relative to the amount of apoptotic and/or necrotic cells prior to the step of administering the pharmaceutical composition, is indicative that cell death is being prevented or reduced in the osteonecrotic tissue.

In some embodiments, the pharmaceutical composition comprises a conjugate of LLP2A and Alendronate ("LLP2A-Ale") having the formula:

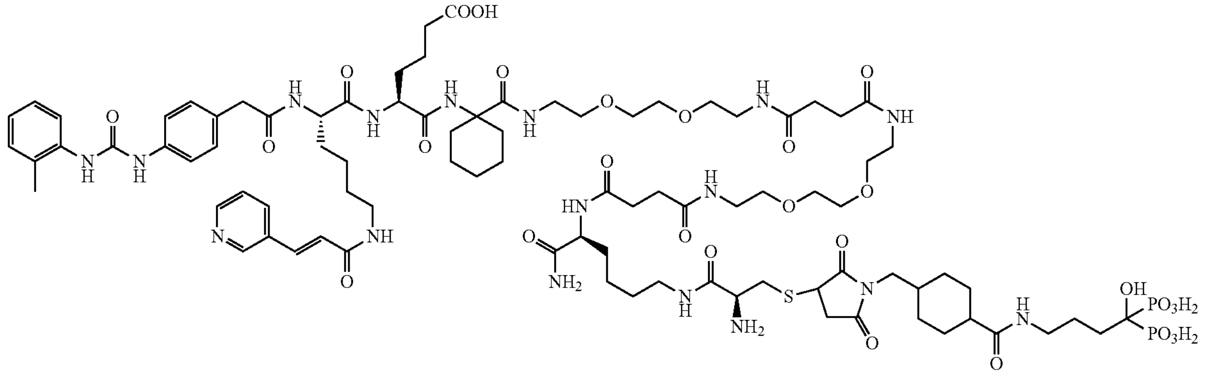

In some embodiments, the osteonecrosis is traumatic osteonecrosis. In some embodiments, the osteonecrosis is glucocorticoid-induced osteonecrosis or alcohol-induced osteonecrosis. In some embodiments, the at least one bone is a femur, hip, knee, shoulder, ankle, wrist, or jaw bone.

In some embodiments, the step of identifying the subject having at least one osteonecrotic lesion in at least one bone comprises magnetic resonance imagining of the at least one bone. In some embodiments, the identifying step comprises detecting at least one osteonecrotic lesion having a size of at least 3.5 $cm^2$. In some embodiments, the identifying step comprises detecting at least one osteonecrotic lesion having a size of at least 5 $cm^2$.

In some embodiments, the method further comprises administering exogenous mesenchymal stem cells. In some embodiments, the pharmaceutical composition and the exogenous mesenchymal stem cells are administered concurrently. In some embodiments, the pharmaceutical composition and the exogenous mesenchymal stem cells are administered sequentially.

In some embodiments, one or both of the pharmaceutical composition and the mesenchymal stem cells are administered by injection. In some embodiments, one or both of the pharmaceutical composition and the mesenchymal stem cells are administered in a series of doses separated by intervals of days or weeks.

In some embodiments, the subject is a human. In some embodiments, the subject is a non-human mammal. In some embodiments, the subject is an adult. In some embodiments, the subject is a juvenile.

In another aspect, uses of a pharmaceutical composition comprising a conjugate of an LLP2A peptidomimetic ligand and a bisphosphonate drug for the treatment of osteonecrosis, for the increasing of vascular density in an osteonecrotic tissue, and/or for the preventing or reducing cell death in an osteonecrotic tissue are provided. In some embodiments, the pharmaceutical composition comprises a conjugate of LLP2A and Alendronate ("LLP2A-Ale") having the formula:

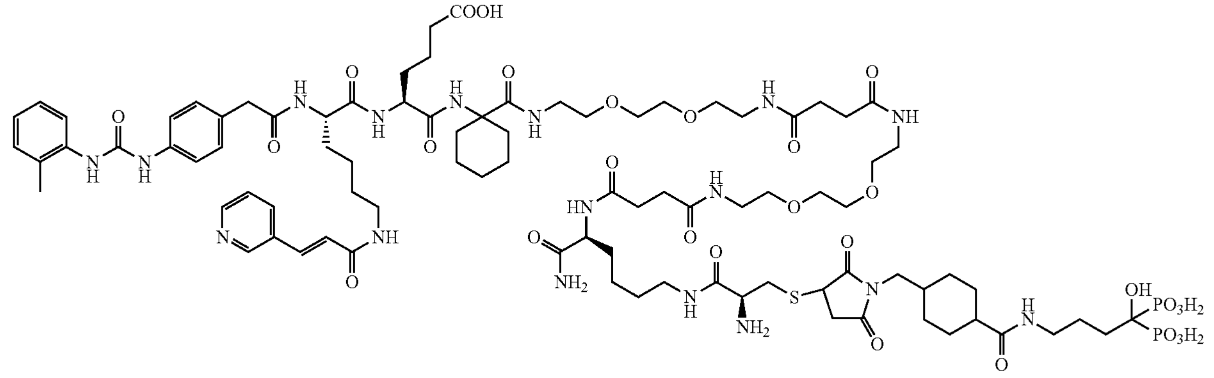

In some embodiments, one or both of the pharmaceutical composition and the exogenous mesenchymal stem cells is administered systemically. In some embodiments, one or both of the pharmaceutical composition and the mesenchymal stem cells are administered locally (e.g., locally at the site of the at least one osteonecrotic lesion). In some embodiments, the site of the at least one osteonecrotic lesion is in a femur, hip, knee, shoulder, ankle, wrist, or jaw bone.

In some embodiments, one or both of the pharmaceutical composition and the mesenchymal stem cells are administered intravenously. In some embodiments, one or both of the pharmaceutical composition and the mesenchymal stem cells are administered by injection. In some embodiments, the pharmaceutical composition further comprises exogenous mesenchymal stem cells.

In still another aspect, pharmaceutical compositions comprising a conjugate of an LLP2A peptidomimetic ligand and a bisphosphonate drug for the manufacture of a medicament for the treatment of osteonecrosis, for the increasing of vascular density in an osteonecrotic tissue, and/or for the preventing or reducing cell death in an osteonecrotic tissue are provided. In some embodiments, the pharmaceutical composition comprises a conjugate of LLP2A and Alendronate ("LLP2A-Ale") having the formula:

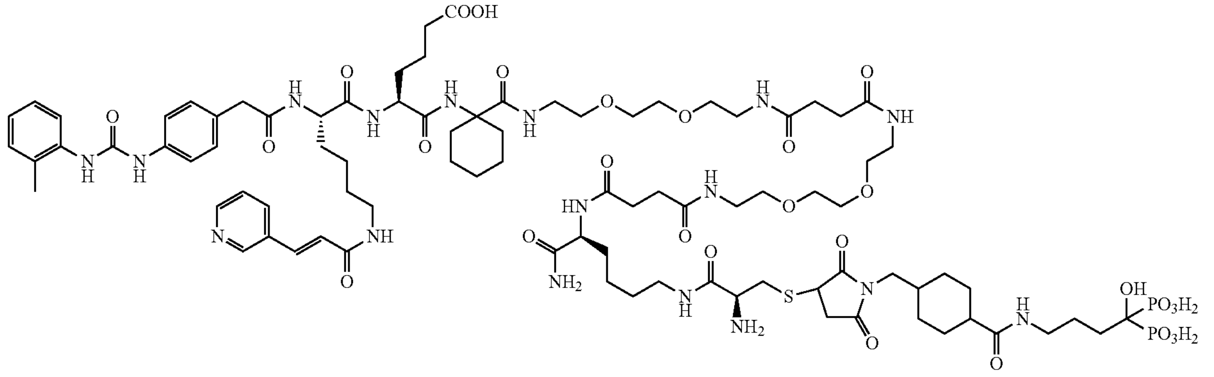

In some embodiments, the pharmaceutical composition further comprises exogenous mesenchymal stem cells.

Ale, Dex+500 μg/kg LLP2A-Ale, or Dex+750 μg/kg LLP2A-Ale as described above for FIG. 7 were assessed for empty lacunae density within the distal femoral epiphysis region. Empty lacunae density was calculated by determining the number of empty lacunae in the entire distal femoral epiphysis region divided by the total number of osteocytes within the same region for each specimen. In the Dex only group, 75% of the samples had 10% or more empty lacunae, as compared to 44-62% of the samples in LLP2A-Ale-treated groups. A higher number of LLP2A-Ale 250 μg/kg, LLP2A-Ale 500 μg/kg, and LLP2A-Ale 750 μg/kg—treated samples had less than 10% empty lacunae as compared to Dex only treatment.

Figures 9A, 9B:
Figure 9D:
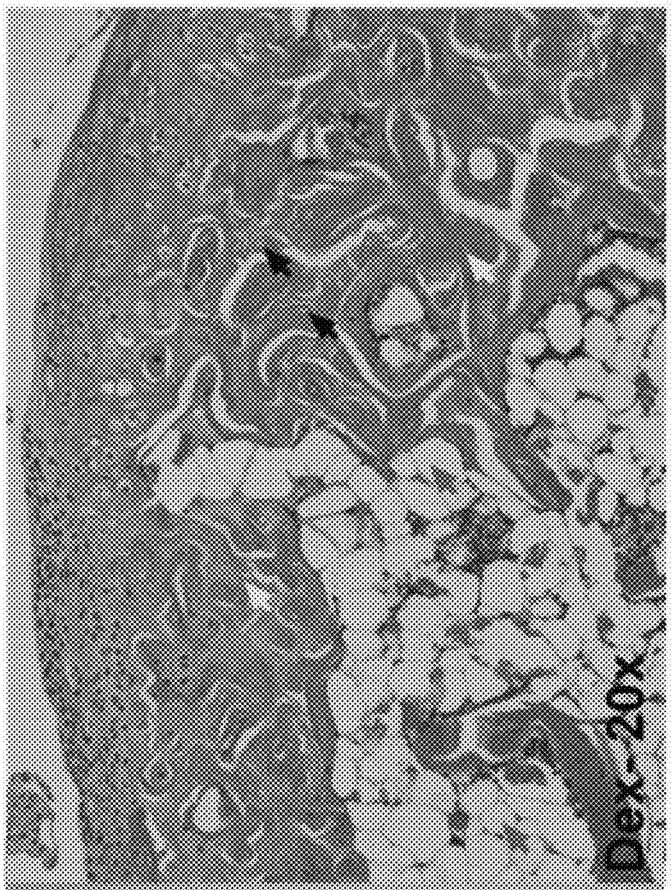
Figure 9C:
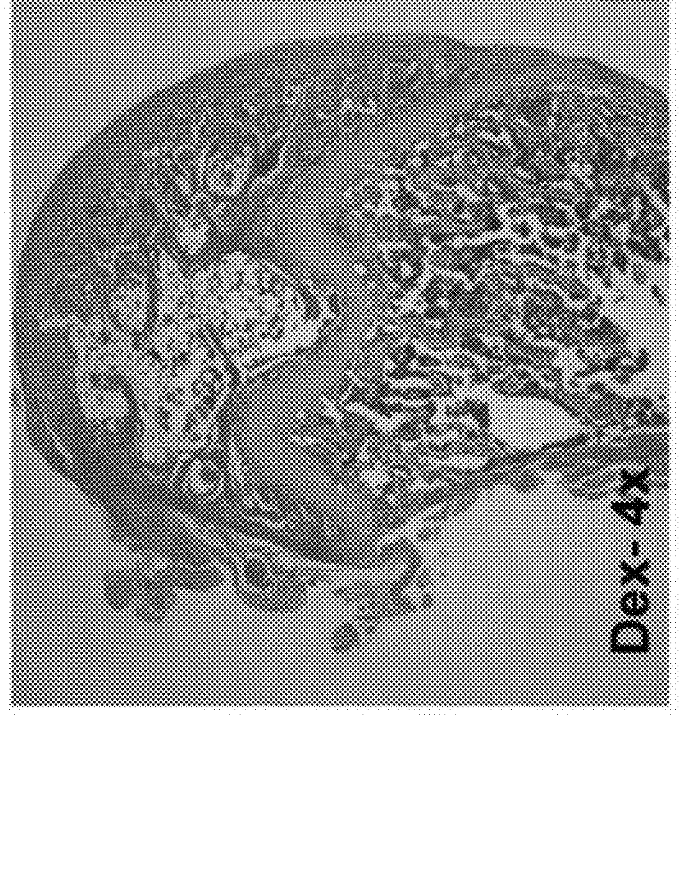
Figure 9E:
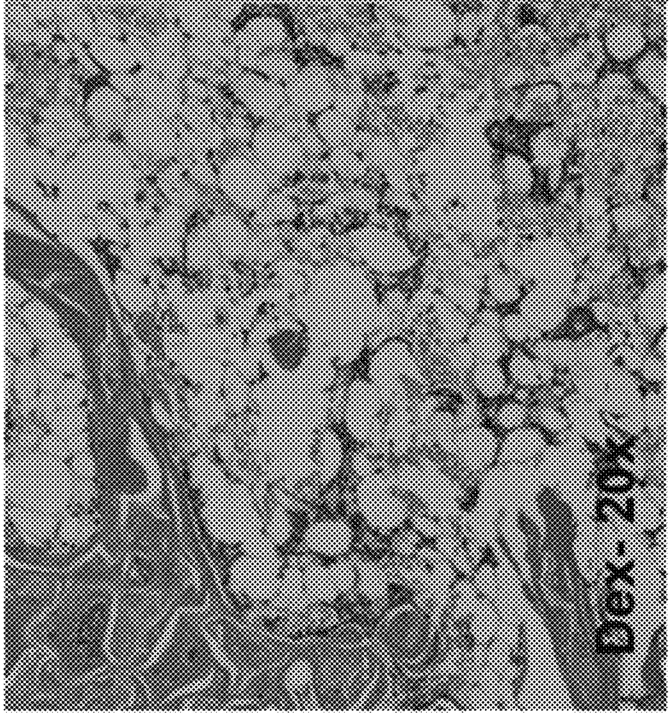
Figure 9F:
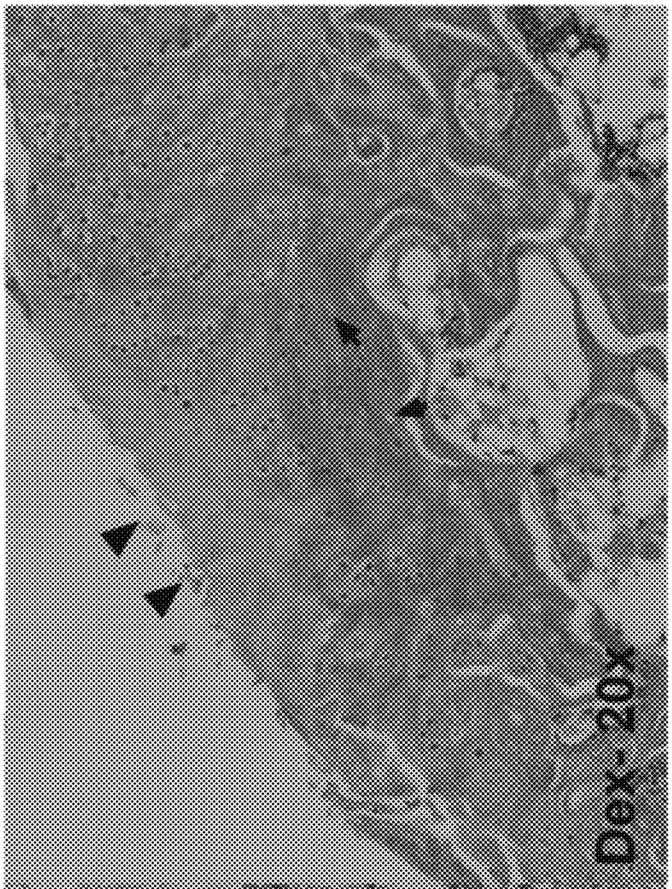

FIG. 9A-9F. Histological evaluation of femurs from placebo- or dexamethasone-treated mice. Mice were treated with placebo (PL) or dexamethasone alone (Dex) as described above for FIG. 7. All mice were euthanized at day 90. Right and left distal femurs were fixed in 10% neutral buffer formalin and decalcified. The specimens were dehydrated, embedded in paraffin, cut into 5 micron sections and H&E stained. The sections were scored by two experienced histologists and then a consensus reading was performed by two additional histologists. FIG. 9A-9B: 4× (A) and 20× (B) magnifications of representative proximal femoral epiphyses in mice treated with placebo. (C) 4× magnification of a representative proximal femoral epiphyses in mice treated with dexamethasone (Dex) alone. FIGS. 9D, 9E, and 9F: 20× magnifications of representative proximal femoral epiphyses in mice treated with dexamethasone (Dex) alone. In dexamethasone treated mice, most of the bone marrow space was occupied by fat (blue arrows in (D-F)), developed necrotic bone marrow (green arrows in (E)), and trabeculae, characterized by empty lacunae (black arrows), pyknotic nuclei of osteocytes (yellow arrows in (D)) and surrounded by necrotic fat debris.

Figure 10A:
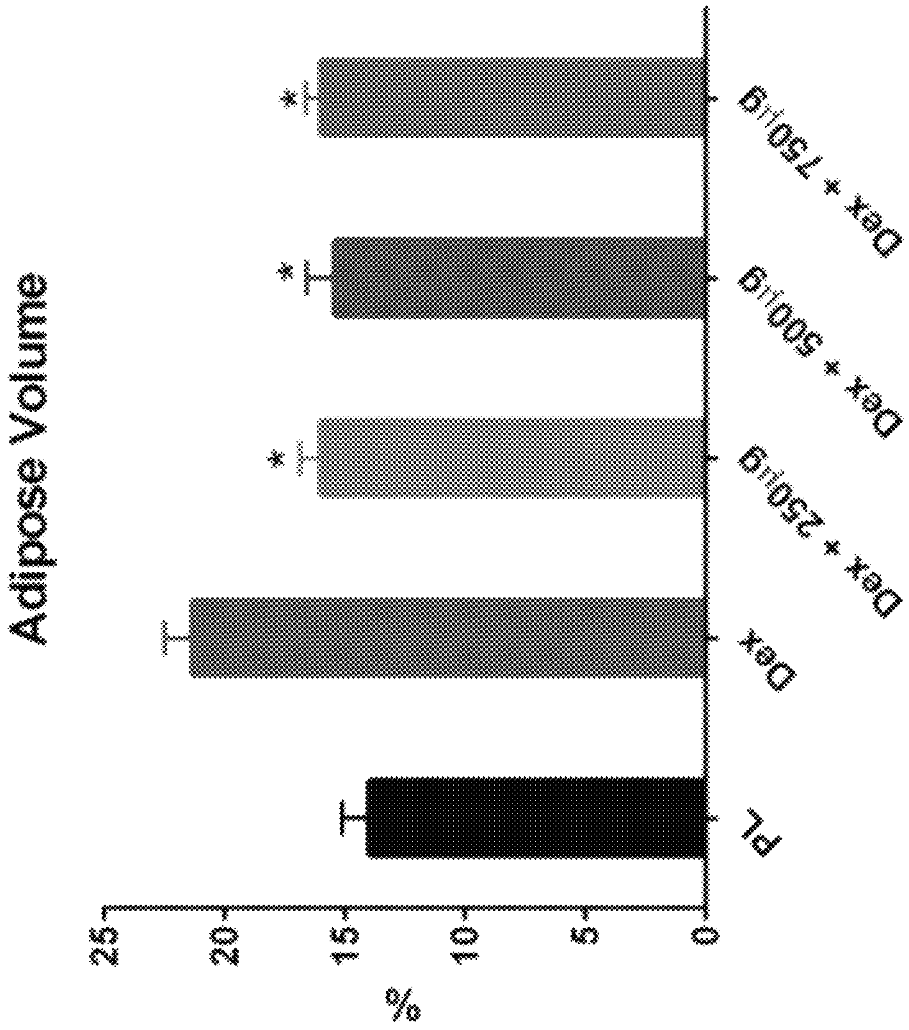
Figure 10B:
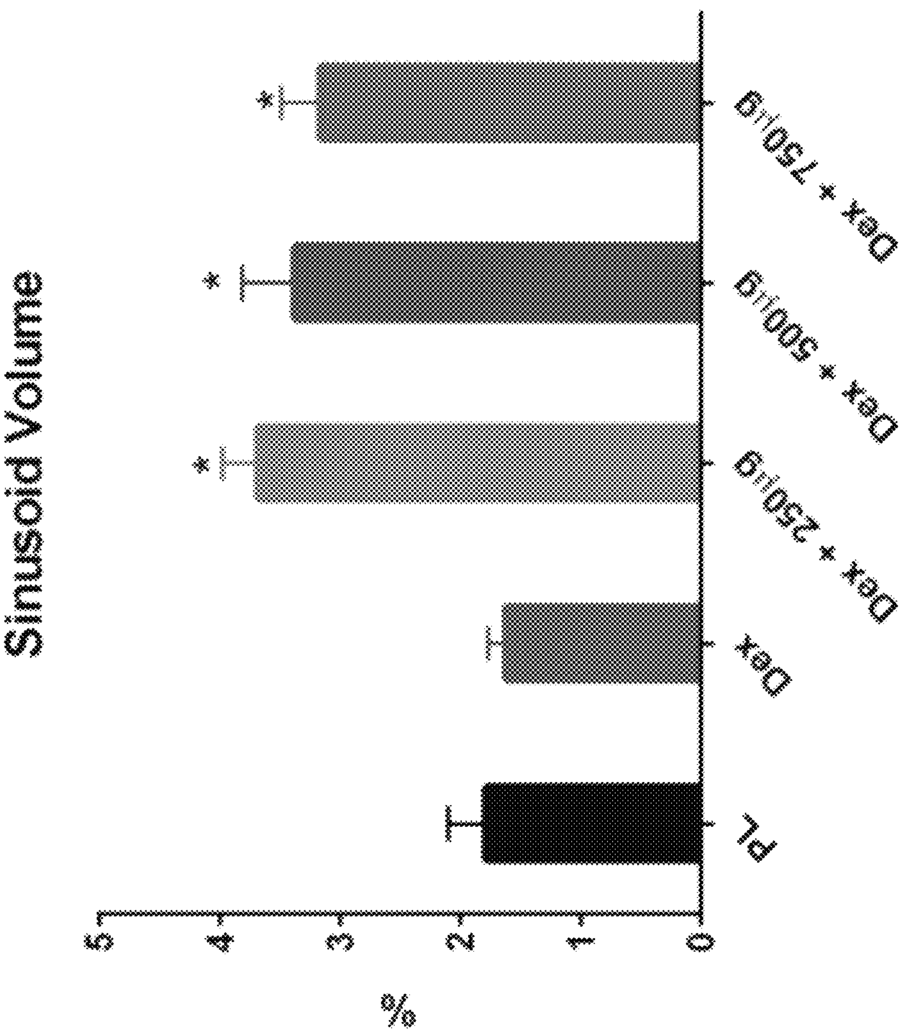

FIG. 10A-10B. Adipose and sinusoid volume of femurs from treated mice. Mice were treated with placebo (PL), dexamethasone alone (Dex), Dex+250 μg/kg LLP2A-Ale, Dex+500 μg/kg LLP2A-Ale, or Dex+750 μg/kg LLP2A-Ale as described above for FIG. 7. (A) Mice were assessed for adipose volume within the distal femoral epiphysis region. Mice receiving LLP2A-Ale treatments had reduced adipose volumes as compared to mice treated with Dex alone. (B) Mice were assessed for sinusoids in the bone marrow. Mice receiving LLP2A-Ale treatments had increased sinusoid volumes as compared to mice treated with Dex alone or placebo. * $p<0.05$ from Dex+LLP2A-Ale treatment at day 90 study.

FIG. 11A-11F. Histological evaluation of femurs from LLP2A-Ale-treated mice. Mice were treated with Dex+250 μg/kg LLP2A-Ale as described above for FIG. 7. All mice were euthanized at day 90. Right and left distal femurs were fixed in 10% neutral buffer formalin and decalcified. The specimens were dehydrated, embedded in paraffin, cut into 5 micron sections and H&E stained. The sections were scored by two experienced histologists and then a consensus reading was performed by two additional histologists. (A, D): 4× magnifications of representative proximal femoral epiphyses in mice treated with Dex+LLP2A-Ale. (B, C, E, F): 20× magnifications of representative proximal femoral epiphyses in mice treated with Dex+LLP2A-Ale. In the LLP2A-Ale treated mice, an increase in sinusoid formation was observed, projecting into necrotic bone marrow (B) or occupied in bone marrow where no bone marrow necrosis was noted (E-F). Some osteoblasts were observed at the trabecular bone surface and close to the sinusiods (yellow arrow heads in (E)).

Figure 12:
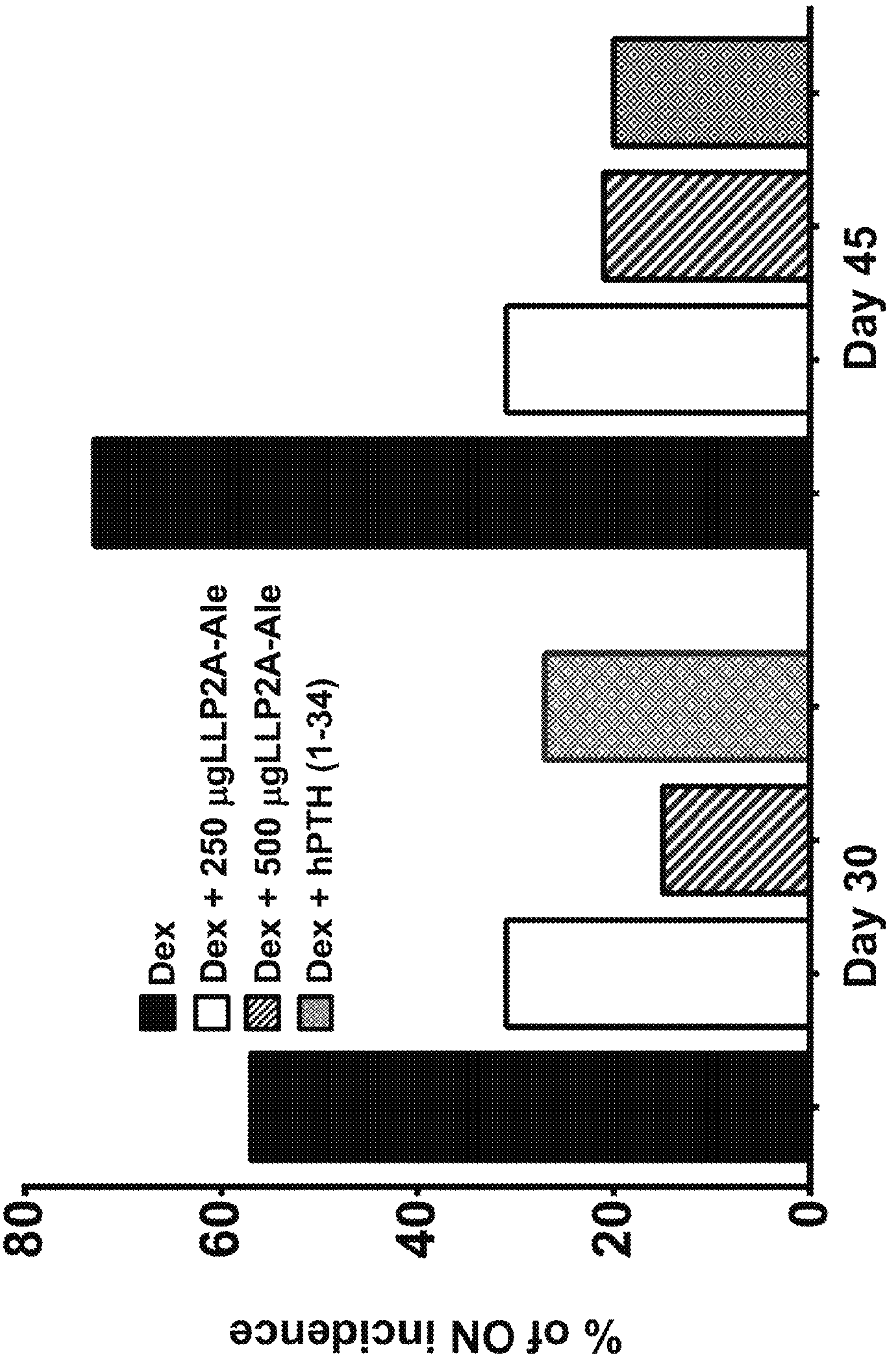

FIG. 12. Reduction in incidence of glucocorticoid-induced osteonecrosis in mice treated with recombinant LLP2A-Ale. Mice were randomized into placebo (PL) (fresh water), dexamethasone (Dex) 4 mg/l in drinking water, Dex+250 μg/kg LLP2A-Ale, Dex+500 μg/kg LLP2A-Ale, or Dex+40 μg/kg hPTH (1-34) groups for a 30 day treatment period or a 45 day treatment period. The incidence of Dex-induced osteonecrosis was 57% on day 30 and 73% on day 45. Both LLP2A-Ale (both doses) and hPTH (1-34) treatment prevented glucocorticoid-induced osteonecrotic lesions.

DETAILED DESCRIPTION OF THE INVENTION

I. Introduction

Osteonecrosis is a bone disease that results from the temporary or permanent loss of blood supply to the bone. Without an adequate blood supply, the bone tissue dies, and can ultimately lead to the collapse of the bone and surrounding joints.

As described herein, it has been found that LLP2A-Ale conjugates are able to prevent the loss of blood supply to bone, and increase the vascularity of bone in an animal model of glucocorticoid-induced osteonecrosis. LLP2A-Ale conjugates are also able to prevent the death of osteocytes, and furthermore, can increase the formation of new bone in an animal model of glucocorticoid-induced osteonecrosis.

Thus, in one aspect, methods of preventing and/or treating osteonecrosis, comprising the administration of a pharmaceutical composition of a peptidomimetic ligand (e.g., LLP2A) conjugated to a bisphosphonate drug (e.g., alendronate) are provided. In another aspect, methods of increasing vascular density in an osteoporotic tissue, comprising the administration of a pharmaceutical composition of a peptidomimetic ligand (e.g., LLP2A) conjugated to a bisphosphonate drug (e.g., alendronate) are provided. In yet another aspect, methods of methods of reducing or preventing cell death in an osteonecrotic tissue, comprising the administration of a pharmaceutical composition of a peptidomimetic ligand (e.g., LLP2A) conjugated to a bisphosphonate drug (e.g., alendronate) are provided. In some embodiments, the peptidomimetic ligand-bisphosphonate drug conjugate is administered in combination with mesenchymal stem cells and/or an anabolic agent such as PTH.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular biology, and chemistry described below are those well-known and commonly employed in the art.

As used herein, the terms "a" or "an," when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

As used herein, the term "Ale" or "Alen" refers to Alendronate.

As used herein, the term "peptide" refers to a compound made up of a single chain of D- or L-amino acids or a mixture of D- and L-amino acids joined by peptide bonds. Generally, peptides are about 2 to about 50 amino acids in length. Preferably, a peptide is about 2 to about 25 amino acids in length, about 3 to 20 amino acids in length, or about 3 to 10 amino acids in length.

As used herein, the term "amino acid" refers to naturally occurring, unnatural, and synthetic amino acids, as well as amino acid analogs and amino acid mimetics that function in a manner similar to the naturally occurring amino acids. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic carboxylic acids (acetic acid, propionic acid, glutamic acid, citric acid and the like), organic sulfonic acids (methanesulfonic acid), salts, quaternary ammonium (methyl iodide, ethyl iodide, and the like) salts. Pharmaceutically acceptable salts include salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the terms "pharmaceutically acceptable excipient" and "pharmaceutically acceptable carrier" refer to a substance that aids the administration of an active agent to and absorption by a subject. "Pharmaceutically acceptable excipient" refers to an excipient that can be included in a composition as described herein and that causes no significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients can also be used.

As used herein, the term "hydrate" refers to a compound that is complexed to at least one water molecule. In some embodiments, an LLP2A-bisphosphonate compound as described herein can be complexed with from 1 to 10 water molecules.

As used herein, the term "isomers" refers to compounds with the same chemical formula but which are structurally distinguishable.

As used herein, the term "mesenchymal stem cell" refers to a multipotent stem cell (i.e., a cell that has the capacity to differentiate into a subset of cell types) that can differentiate into a variety of cell types, including osteoblasts, chondrocytes, and adipocytes. Mesenchymal stem cells can be obtained from a variety of tissues, including but not limited to bone marrow tissue, adipose tissue, muscle tissue, birth tissue (e.g., amnion, amniotic fluid, or umbilical cord tissue), skin tissue, bone tissue, and dental tissue.

As used herein, the term "subject" refers to a living organism having or prone to a condition that can be treated by administration of a pharmaceutical composition as provided herein (e.g., one who has been diagnosed with an osteonecrotic lesion, who is suspected of having an osteonecrotic lesion, or who is at risk of having an osteonecrotic lesion). Non-limiting examples include humans, other mammals, and other non-mammalian animals, As used herein, the term "therapeutically effective amount" refers to an amount of a pharmaceutical composition (e.g., a conjugate comprising LLP2A peptidomimetic ligand and a bisphosphonate drug and/or stem cells as described herein) useful for treating or ameliorating an identified disease or condition, or for exhibiting a detectable therapeutic or inhibitory effect. The effect can be detected by any assay method known in the art.

As used herein, the terms "treat," "treating," and "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; and/or improving a patient's physical or mental well-being. The treatment or amelioration of symptoms can be based on objective or subjective parameters, including but not limited to the results of a physical examination and/or a biological assay performed on a sample from the subject.

III. Compositions for the Treatment of Osteonecrosis

In one aspect, the present invention relates a peptidomimetic ligand, e.g., LLP2A, conjugated with a bisphosphonate, e.g., alendronate, which can be used, alone or in combination with mesenchymal stem cells and/or an anabolic agent, for preventing and/or treating osteonecrosis, for increasing vascular density in an osteonecrotic tissue, or for preventing or reducing cell death in an osteonecrotic tissue.

LLP2A-Bisphosphonate Conjugates

In some embodiments, the peptidomimetic ligand is an LLP2A compound having the following structure:

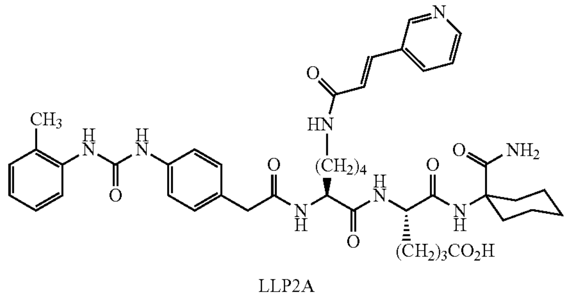

LLP2A

LLP2A is a high-affinity, high-specificity peptidomimetic ligand that binds the α4β1 integrin. See, Liu et al., *Biopolymers,* 84:595-604 (2006); Peng et al., *Nature Chemical Biology* 2:381-389 (2006); DeNardo et al., *J. Nucl. Med.* 50:625-634 (2009).

In some embodiments, the LLP2A peptidomimetic ligand is conjugated to a bisphosphonate. Bisphosphonates are a class of drugs having two phosphonate groups, which have been used for the treatment of osteoporosis and for the prevention of bone loss. Bisphosphonates comprise two phosphonate groups that are covalently linked to a carbon. Bisphosphonates may be nitrogen-containing (e.g., etidronate) or non-nitrogen containing (e.g., alendronate). Suitable bisphosphonate drugs for use in conjugating to a peptidomimetic ligand include, but are not limited to, Etidronate (Didronel®), Clodronate (Bonefos®, Loron®), Tiludronate (Skelid®), Pamidronate (Aredia®), Neridronate, Olpadronate, Alendronate (Fosamax®), Ibandronate (Boniva®), Risedronate (Actonel®) and Zoledronate (Zometa®, Reclast®). One of skill in the art will appreciate that other bisphosphonates are useful in the present invention. In some embodiments, the bisphosphonate is alendronate.

In some embodiments, the pharmaceutical composition comprises a compound of Formula I (e.g., LLP2A-Ale):

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In some embodiments, a compound as described herein can exist in unsolvated forms as well as solvated forms, including hydrated forms. In general, the solvated forms are equivalent to unsolvated forms and are encompassed within the scope of the present invention. Certain compounds may exist in multiple crystalline or amorphous forms. In general, all physical forms are equivalent for the uses contemplated by the present invention and are intended to be within the scope of the present invention.

In some embodiments, a compound as described herein possesses asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present (I)

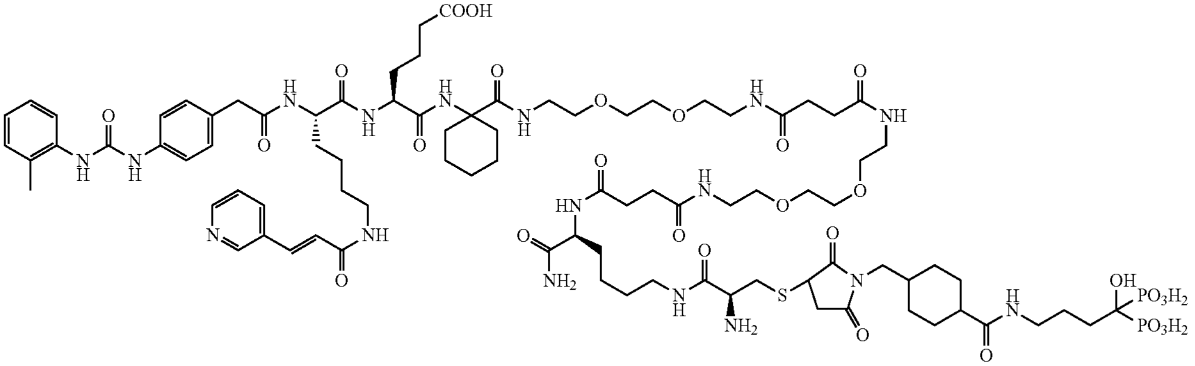

LLP2A-Ale

In some embodiments, the pharmaceutical composition comprises a salt, hydrate, solvate, prodrug form, isomer, or metabolite of an LLP2A compound conjugated to a bisphosphonate drug (e.g., a compound of Formula I).

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, lithium salts, and potassium salts; alkaline earth metal salts such as calcium salts, and magnesium salts; aluminum salts; and ammonium salts, such as ammonium, trimethyl-ammonium, diethylammonium, and tris-(hydroxymethyl)-methyl-ammonium salts. Other salts with organic bases include salts with diethylamine, diethanolamine, meglumine, and N,N'-dibenzylethylenediamine.

invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

In some embodiments, the compound is in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds as described herein can be synthesized by a variety of methods known to one of skill in the art (see *Comprehensive Organic Transformations* by Richard C. Larock, 1989) or by an appropriate combination of generally well known synthetic methods. Techniques useful in synthesizing the compounds of the invention are both readily apparent and accessible to those of skill in the relevant art. As a non-limiting example, LLP2A-Alendronate (LLP2A-Ale) can be made by conjugate addition of the sulfhydryl group of LLP2A-Lys (D-Cys) to alendronate-maleimide (Ale-Mal). The latter can be prepared in situ from alendronate and sulfosuccinimidyl-4-(N-maleimidomethyl) cyclohexane-1-carboxylate (sulfo-SMCC). LLP2A-Lys (D-Cys) can be prepared by solid phase synthesis from several commercially available starting materials and one characterized intermediate, 4-[(N'-2-methylphenyl) ureido] phenylacetic acid (UPA), which can also prepared from commercially available starting materials. Methods of making LLP2A compounds conjugated to a bisphosphonate drug, including a detailed description of the synthesis of LLP2A-Ale, are found in, e.g., International Appl. Pub. Nos. WO 2012/031228 and WO 2013/032527, the disclosures of which are herein incorporated in their entirety for all purposes.

Mesenchymal Stem Cells

In some embodiments, a pharmaceutical composition comprising a conjugate of an LLP2A peptidomimetic ligand and a bisphosphonate drug (e.g., LLP2A-Ale) is co-administered with mesenchymal stem cells (MSCs) for treating osteonecrosis, for increasing vascular density in an osteonecrotic tissue, or for preventing or reducing cell death in an osteonecrotic tissue.

The mesenchymal stem cells that are administered may be a homogeneous composition or may be a mixed cell population comprising MSCs or enriched for MSCs. Suitable MSCs may be obtained or derived, e.g., from bone marrow mononuclear cells collected from aspirates of bone marrow. In some embodiments, homogeneous mesenchymal stem cell compositions are obtained by culturing adherent marrow or periosteal cells in an appropriate culture medium, and the mesenchymal stem cell compositions may be obtained by culturing adherent marrow or periosteal cells to obtain an expanded MSC population. The MSCs may be identified by specific cell surface markers which are identified with unique monoclonal antibodies. A method for obtaining a cell population enriched in mesenchymal stem cells is described, for example, in U.S. Pat. No. 5,486,359, incorporated by reference herein. Sources for mesenchymal stem cells include, but are not limited to, bone marrow, muscle, adipose, placental tissue, umbilical cord tissue, tooth pulp, skin tissue, peripheral blood, and synovial membranes. Mesenchymal stem cells (MSCs) may be purified using methods known in the art (see, e.g., Wakitani et al., 1995; Fukuda and Yuasa, 2006; Woodbury et al., 2000; Deng et al., 2001; Kim et al., 2006; Mareschi et al., 2006; Krampera et al., 2007).

Compositions that are enriched for MSCs (e.g., having greater than about 95%, usually greater than about 98%, of mesenchymal stem cells) can be achieved using techniques for isolation, purification, and culture expansion of mesenchymal stem cells that are known in the art. As a non-limiting example, isolated, cultured mesenchymal stem cells may comprise a single phenotypic population (e.g., at least about 95% or about 98% homogeneous) by flow cytometric analysis of expressed surface antigens. The desired cells in such composition are identified as expressing one or more cell surface markers for the cell type (e.g., CD73 or CD105).

The mesenchymal stem cells may be from a spectrum of sources including autologous, allogeneic, or xenogeneic.

In some embodiments, the mesenchymal stem cells are administered in an amount of from about $1\times10^4$ cells/kg to about $1\times10^8$ cells/kg of body weight (e.g., about 1×104 cells/kg, about $1\times10^5$ cells/kg, about $1\times10^6$ cells/kg, about $1\times10^7$ cells/kg, or about $1\times10^8$ cells/kg). The amount of mesenchymal stem cells to be administered is dependent upon a variety of factors, including the age, weight, and sex of the patient.

The mesenchymal stem cells may be administered in conjunction with an acceptable pharmaceutical carrier. For example, the mesenchymal stem cells may be administered as a cell suspension in a pharmaceutically acceptable liquid medium or gel for injection or topical application. In one embodiment, the pharmaceutically acceptable liquid medium is a saline solution. The saline solution may contain additional materials such as dimethylsufoxide (DMSO) and human serum albumin.

Anabolic Agents

In some embodiments, a pharmaceutical composition comprising a conjugate of an LLP2A peptidomimetic ligand and a bisphosphonate drug (e.g., LLP2A-Ale) is co-administered with an anabolic agent for treating osteonecrosis, for increasing vascular density in an osteonecrotic tissue, or for preventing or reducing cell death in an osteonecrotic tissue.

As used herein, an anabolic agent is an agent that stimulates or promotes the formation of new bone. Suitable anabolic agents for use in combination with an LLP2A-bisphosphonate conjugate include, but are not limited to, parathyroid hormone (PTH), growth hormone (GH), insulin-like growth factor-I (IGF-I), parathyroid hormone-related peptide (PTHrp), or anti-sclerostin antibody. In some embodiments, the anabolic agent is PTH or an analog thereof. In some embodiments, the anabolic agent is a recombinant form of PTH (e.g., PTH 1-34 (Teriparatide)).

An anabolic agent may be administered in conjunction with an acceptable pharmaceutical carrier as described herein. For example, in some embodiments, an anabolic agent may be formulated for administration by injection, or by oral, parenteral, or nasal administration.

Formulation and Administration

In some embodiments, the compositions described herein (e.g., compositions comprising a conjugate of an LLP2A peptidomimetic ligand and a bisphosphonate drug (e.g., LLP2A-Ale), mesenchymal stem cells, and/or anabolic agents) are provided as a pharmaceutical composition comprising a pharmaceutically acceptable carrier or excipient. Details on techniques for formulation and administration are well described in the scientific and patent literature, see, e.g., the latest edition of Remington's Pharmaceutical Sciences, Mack Publishing Co, Easton PA.

For preparing pharmaceutical compositions as described herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In general, the type of carrier is selected based on the mode of administration. For example, in some embodiments, oral preparations include tablets, pills, powder, dragees, capsules, liquids, lozenges, cachets, gels, syrups, slurries, suspensions, etc., suitable for ingestion by the patient. In some embodiments, a pharmaceutical composition for oral administration or delivery by injection can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions typically include a conventional pharmaceutical carrier or excipient and may additionally include other medicinal agents, carriers, adjuvants, diluents, tissue permeation enhancers, solubilizers, and the like. In some embodiments, the composition contains about 0.01% to about 90%, e.g., about 0.1% to about 75%, about 0.1% to 50%, or about 0.1% to 10% by weight of a conjugate, mesenchymal stem cells, and/or anabolic agent, with the remainder consisting of suitable pharmaceutical carrier and/or excipients. Appropriate excipients can be tailored to the particular composition and route of administration by methods well known in the art, e.g., Remington's Pharmaceutical Sciences, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethylcellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compound or compounds and on the particular physio-chemical characteristics of the compounds.

Generally, such carriers should be nontoxic to recipients at the dosages and concentrations employed. Ordinarily, the preparation of such compositions entails combining the compound or compounds with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations can also be used orally using, for example, push-fit capsules made of gelatin, as well as soft, sealed capsules made of gelatin and a coating such as glycerol or sorbitol. Push-fit capsules can contain compounds mixed with fillers or binders such as lactose or starches, lubricants such as talc or magnesium stearate, and, optionally, stabilizers. In soft capsules, the compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. Liquid compositions can be prepared, e.g., by dissolving or dispersing a conjugate and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound or compounds described herein in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto,

*J. Pharmacol. Exp. Ther.* 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

In some embodiments, the pharmaceutical composition is a slow release formulation. Slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly (methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of LLP2A-bisphosphonate conjugates, mesenchymal stem cells, and/or anabolic agent. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds in a sustained release formulation.

Methods for preparing such dosage forms are known to those skilled in the art (see, for example, Remington's Pharmaceutical Sciences, supra. The composition to be administered contains a quantity of the LLP2A-bisphosphonate conjugates, mesenchymal stem cells, and/or anabolic agents in a pharmaceutically effective amount for relief of a condition being treated when administered in accordance with the teachings of this invention. In addition, pharmaceutically acceptable salts of the conjugates described herein (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4th Ed. (New York: Wiley-Interscience, 1992).

In some embodiments, the LLP2A-bisphosphonate conjugates, mesenchymal stem cells, and/or anabolic agents are administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

In some embodiments, co-administration of a LLP2A-bisphosphonate conjugate with mesenchymal stem cells and/or an anabolic agent enhances the therapeutic effects such that administration of one or more of the LLP2A-bisphosphonate conjugate, the mesenchymal stem cells, or anabolic agent can be administered at a reduced amount or at a reduced frequency relative to the amount and/or frequency that would be required to induce a therapeutic effect if administered alone. For example, in some embodiments, one or more of the LLP2A-bisphosphonate conjugate, the mesenchymal stem cells, and the anabolic agent can be administered 10%, 20%, 30%, 40%, 50%, 60%, or 70% less often than if administered alone. In some embodiments, one or more of the LLP2A-bisphosphonate conjugates, the mesenchymal stem cells, and the anabolic agent can be administered in an amount that is about 10%, 20%, 30%, 40%, 50%, 60%, or 70% less than the amount that would be required to induce a therapeutic effect if the LLP2A-bisphosphonate conjugate or the mesenchymal stem cells were administered alone.

In practicing the methods described herein, the pharmaceutical compositions can be used alone, or in combination with other therapeutic or diagnostic agents. Where multiple compositions are used for a therapeutic protocol, the compositions can be administered separately or the compositions can be administered together, such as in an admixture. Where one or more compositions are administered separately, the timing and schedule of administration of each composition can vary. The other therapeutic or diagnostic agents can be administered at the same time as the compounds of the present invention, separately or at different times.

In some embodiments, co-administration of the compositions (e.g., a LLP2A-bisphosphonate conjugate as described herein along with one or more of mesenchymal stem cells and anabolic agents) includes administering one composition within 0.5, 1, 2, 4, 6, 8, 10, 12, 16, 20, or 24 hours of a second composition. In some embodiments, the two compositions are administered simultaneously, approximately simultaneously (e.g., within about 1, 5, 10, 15, 20, or 30 minutes of each other), or sequentially in any order. In some embodiments, co-administration can be accomplished by co-formulation, e.g., preparing a single pharmaceutical composition including both the LLP2A-Ale conjugates and the mesenchymal stem cells and/or anabolic agent. In other embodiments, the compositions can be formulated separately.

Administration of the compounds of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. In some embodiments, one or more of the LLP2A-bisphosphonate conjugates, mesenchymal stem cells, and anabolic agents are administered locally, e.g., to a bone (e.g., a femur, hip, knee, shoulder, ankle, wrist, or jaw bone) or at the site of an osteonecrotic lesion within a bone (e.g., a femur, hip, knee, shoulder, ankle, wrist, or jaw bone). In some embodiments, one or more of the LLP2A-bisphosphonate conjugates, the mesenchymal stem cells, and anabolic agents are administered systemically. In some embodiments, the compositions are administered by different routes. For example, in some embodiments, one composition (e.g., an LLP2A-bisphosphonate conjugate) is administered locally, while another composition (e.g., mesenchymal stem cells or an anabolic agent) is administered systemically.

IV. Methods of Preventing or Treating Osteonecrosis, Increasing Vascular Density in an Osteonecrotic Tissue, and Reducing Cell Death in an Osteonecrotic Tissue In one aspect, the compositions described herein (e.g., compositions comprising a conjugate of an LLP2A peptidomimetic ligand and a bisphosphonate drug (e.g., LLP2A-Ale)) are used for preventing and/or treating osteonecrosis, for increasing vascular density, or for reducing cell death in an osteonecrotic tissue. In some embodiments, the method comprises:

administering to the subject a pharmaceutical composition comprising a conjugate of an LLP2A peptidomimetic ligand and a bisphosphonate drug.

In some embodiments, the method comprises:

identifying a subject having or suspected of having osteonecrosis in at least one bone; and administering to the subject a pharmaceutical composition comprising a conjugate of an LLP2A peptidomimetic ligand and a bisphosphonate drug.

In some embodiments, the method comprises administering a pharmaceutical composition comprising a conjugate of LLP2A and Alendronate ("LLP2A-Ale") as shown in Formula I above. In some embodiments, the method further comprises administering mesenchymal stem cells, e.g., concurrently or sequentially with the conjugate. In some embodiments, the method further comprises administering one or more anabolic agents (e.g., Teriparatide), e.g., concurrently or sequentially with the conjugate.

In some embodiments, the subject is an adult or juvenile subject who has been identified as having osteonecrosis. In some embodiments, the subject is an adult or juvenile subject who is suspected of having osteonecrosis. In some embodiments, the subject is an adult. In some embodiments, the subject is a juvenile.

Osteonecrosis, which is also called avascular necrosis or aseptic necrosis, is the death of bone cells in a bone due to decreased blood flow. If untreated, the death of the bone cells in the bone can lead to the collapse of areas of bone, which in turn, can lead to degenerative arthritis of joints near the bone. Osteonecrosis most commonly affects the hips and knees, but also can affect the shoulders, wrists, hands, ankles, feet, and jaw.

Osteonecrosis can have various causes, including traumatic and non-traumatic causes. Typically in traumatic osteonecrosis, a serious trauma to a bone interrupts the bone's blood supply. Non-traumatic osteonecrosis may result from certain medications, such as corticosteroid medications (e.g., prednisone, cortisone, dexamethasone, or methylprednisolone), particularly when a high dose of the medication is administered for a prolonged period of time; from excessive alcohol consumption; from radiation therapy; or as a result of a disease or condition. See, e.g., Xie et al., 2015, Journal of Orthopaedic Translation, 3:58-70, incorporated by reference herein. In some embodiments, the subject has post-traumatic osteonecrosis (e.g., osteonecrosis that occurs following a fracture or dislocation of a bone). In some embodiments, the subject has non-traumatic osteonecrosis. In some embodiments, the subject has steroid induced osteonecrosis (e.g., high dose steroid treatment induced osteonecrosis or glucocorticoid induced osteonecrosis), alcohol induced osteonecrosis, or smoking induced osteonecrosis. In some embodiments, the subject has osteonecrosis that is induced as a secondary cause of another disease or condition, including but not limited to, Legg-Calvé-Perthes disease, Caisson disease, sickle cell disease, post-irradiation, chemotherapy, arterial disease, Gaucher's disease, lipid disturbances, connective tissue disease, pancreatitis, kidney disease, liver disease, or lupus. In some embodiments, the osteonecrosis is idiopathic osteonecrosis.

Osteonecrosis is classified in stages which refer to the extent of the disease progression. In some embodiments, the Ficat classification system can be used to determine the stage of the disease. Other classification systems, such as the University of Pennsylvania system, the Association Research Circulation Osseous (ARCO) system, and the Japanese Orthopaedic Association system, can also be used. See, e.g., Jawad et al., *Clin Orthop Related Res,* 2012, 470:2636-2639, incorporated by reference herein. In the Ficat system, there are five stages of bone necrosis (Stage 0 to Stage 4). Stages 0 to 2 are generally described as "early" stages of osteonecrosis, while Stages 3 and 4 are generally described as "late" stages. In Stage 0, osteonecrosis is preclinical and preradiographic (i.e., not detectable by radiography), although evidence of a defect in the bone may be detected by bone marrow pressure studies or core biopsy. In Stage 1, evidence of an osteonecrotic lesion is visible by MRI, minor osteopenia may be visible by X-ray, and bone scan may indicate increased uptake of a radioactive material to the area of bone, which is indicative of injury to the bone (e.g., a tumor, fracture, or infection). Clinical symptoms of pain in the joint may also be exhibited in Stage 1. In Stage 2, evidence of lesion and abnormality in bone tissue can be detected by MRI, mixed osteopenia, sclerosis, and/or subchondral cysts can be detected by X-ray, and increased uptake of radioactive material can be detected by bone scan; clinical symptoms include pain and stiffness in the joint. In Stage 3, changes in the contour of the bone can be detected (e.g., as a "crescent" sign in the femur) and eventual cortical collapse can be detected by X-ray or MRI. In Stage 4, the end stage of the disease, collapse of the bone and decreased joint space will be detectable.

A combination of diagnostic tools, such as X-ray, MRI, bone scan (bone scintigraphy), bone biopsy, clinical features, and "functional exploration of bone," can be used to correlate symptoms with a stage of bone necrosis. For example, bone marrow pressure can be measured in a region of a bone, and change in bone marrow pressure can be measured by performing a stress test on the bone (e.g., by injecting isotonic saline into the bone, waiting a predetermined amount of time, and then measuring the pressure at a time point after the injection). A bone scan can be performed by intravenously injecting a radioactive material, such as technetium, and imaging the bone. See, e.g., Lichn et al., *European Journal of Orthopaedic Surgery & Traumatology,* 1997, 4:263-265, incorporated by reference herein. MRI (magnetic resonance imaging) is a highly sensitive method for detecting osteonecrosis, and can show segmental areas of low signal intensity that are typical for osteonecrosis. See, e.g., Saini et al., *Clinical Radiology,* 2004, 59:1079-1093, incorporated by reference herein. Computed tomography (CT) scan can also be used for detecting osteonecrosis.

In some embodiments, a subject is identified as having or suspected of having osteonecrosis by examining at least one bone or joint in the subject and classifying the subject according to one of the classification systems described herein (e.g., Ficat or ARCO). In some embodiments, the subject is identified as suspected of having osteonecrosis, wherein the subject does not have a detectable osteonecrotic lesion, but wherein an abnormality of the bone can be detected (e.g., a change in bone pressure). In some embodiments, the subject is a subject classified as having Stage 0 disease by the Ficat classification system.

In some embodiments, the subject is identified as having osteonecrosis where an abnormality in the blood flow, blood pool, and/or osteoblastic activity in at least one bone or joint. In some embodiments, the abnormality is detected by bone scintigraphy.

In some embodiments, the subject is identified as having osteonecrosis where at least one osteonecrotic lesion is detected in at least one bone. In some embodiments, the osteonecrotic lesion is detected by MRI. In some embodiments, the subject is identified as having at least one osteonecrotic lesion having a size of at least 3.5 $cm^2$. In some embodiments, the subject is identified as having at least one osteonecrotic lesion having a size of at least 5 $cm^2$. In some embodiments, the subject has at least one osteonecrotic lesion or abnormality in bone as detected by MRI or bone scan, but does not exhibit decreased bone density as measured by X-ray.

In some embodiments, the subject is a subject classified as having Stage 1 disease by the Ficat classification system. In some embodiments, the subject has at least one osteonecrotic lesion or abnormality in bone as detected by MRI or bone scan, and further exhibits decreased bone density, osteopenia, sclerosis, and/or bone cysts as measured by X-ray. In some embodiments, the subject is a subject classified as having Stage 2 disease by the Ficat classification system.

In some embodiments, the subject exhibits bone flattening, imminent bone collapse, or bone collapse. In some embodiments, the subject is a subject having late-stage osteonecrosis (e.g., Stage 3 or Stage 4 by the Ficat classification system).

In some embodiments, the LLP2A peptidomimetic ligand-bisphosphonate drug conjugates as described herein are used for treating osteonecrosis. In some embodiments, treatment of osteonecrosis is measured by evaluating whether an osteonecrotic bone or joint exhibits a reduction in one or more symptoms of osteonecrosis, such as a decrease in the number or size of osteonecrotic lesions, a decrease in the number or size of sclerotic lesions, a decrease in the amount of cell death in the bone, an increase in the amount of vascularization (e.g., vascular density) in the bone or a reduction in bone marrow adipocyte volume. In some embodiments, following administration of a pharmaceutical composition as described herein (e.g., compositions comprising a conjugate of an LLP2A peptidomimetic ligand and a bisphosphonate drug (e.g., LLP2A-Ale)), the method further comprises examining the osteonecrotic bone or joint of the subject to identify a change in one or more symptoms of osteonecrosis. Thus, in some embodiments, a method of treating osteonecrosis comprises:

identifying a subject having one or more symptoms of osteonecrosis in at least one bone;

administering to the subject a pharmaceutical composition comprising a conjugate of an LLP2A peptidomimetic ligand and a bisphosphonate drug; and examining the at least one bone to identify a change in the one or more symptoms of osteonecrosis relative to prior to the administering step.

In some embodiments, the method comprises identifying a change in more than one symptom of osteonecrosis (e.g., in two, three, four or more symptoms of osteonecrosis).

As a non-limiting example, in some embodiments, the method comprises determining the amount of osteonecrotic lesions in a bone or joint prior and/or measuring the size of one or more osteonecrotic lesions in a bone or joint prior to administration of a pharmaceutical composition as described herein; and then subsequent to the administration of the pharmaceutical composition, the method further comprises determining the number of osteonecrotic lesions and/or measuring the size of one or more osteonecrotic lesions in the bone or joint and comparing the size of the lesion or lesions before and after administration of the pharmaceutical composition. In some embodiments, a decrease in the amount of osteonecrotic lesions and/or the size of the osteonecrotic lesion subsequent to the administering step, relative to prior to the administering step, is indicative that the osteonecrosis is being treated in the subject. In some embodiments, a decrease of at least about 1%, 2%, 3%, 4%, 5%, 6%, 7%, 8%, 9%, 10%, 20%, 30%, 40%, 50%, 60%, 70%, 80%, 90% or more in the size of the osteonecrotic lesion subsequent to the administering step, relative to the size of the osteonecrotic lesion prior to the administering step, is indicative that the osteonecrosis is being treated. In some embodiments, a decrease of at least about 1%, 2%, 3%, 4%, 5%, 6%, 7%, 8%, 9%, 10%, 20%, 30%, 40%, 50%, 60%, 70%, 80%, 90% or more in the number of osteonecrotic lesions in the bone or tissue subsequent to the administering step, relative to the number of osteonecrotic lesions prior to the administering step, is indicative that the osteonecrosis is being treated.

In some embodiments, the LLP2A peptidomimetic ligand-bisphosphonate drug conjugates as described herein are used for increasing vascular density in an osteonecrotic tissue. In some embodiments, increased vascular density comprises an increase in the amount of vascularization in the bone. In some embodiments, increased vascular density comprises an increase in sinusoid formation or sinusoidal red blood cell volume in the bone. In some embodiments, following administration of a pharmaceutical composition as described herein (e.g., compositions comprising a conjugate of an LLP2A peptidomimetic ligand and a bisphosphonate drug (e.g., LLP2A-Ale)), the method further comprises examining the osteonecrotic bone or joint of the subject to identify a change in the amount of vascularization.

In some embodiments, the vascularization of an osteonecrotic tissue is measured by superselective angiography (SSA), digital subtraction arteriography (DSA), Doppler-laser hemodynamic measurement, bone scintigraphy, magnetic resonance imaging (MRI, e.g., dynamic MRI with contrast medium injection), Methods of measuring vascularization in osteonecrotic tissue are described in the art. See, e.g., Ehlinger et al., *Orthopedics & Traumatology: Surgery & Research,* 2001, 97:79-88, incorporated by reference herein. In some embodiments, the vascularization of an osteonecrotic tissue is measured by radionuclide bone scintigraphy. In some embodiments, the vascularization of an osteonecrotic tissue is measured by MRI, e.g., dynamic MRI. In some embodiments, an increase of at least about 0.1%, 0.5%, 1%, 2%, 3%, 4%, 5%, 6%, 7%, 8%, 9%, 10%, 20%, 30%, 40%, 50%, 60%, 70%, 80%, 90% or more in the degree of vascularization in an osteonecrotic tissue (e.g., osteonecrotic bone), relative to the degree of vascularization prior to the administering step, is indicative that vascular density is increased in the osteonecrotic tissue. In some embodiments, an increase of at least about 0.1%, 0.5%, 1%, 2%, 3%, 4%, 5%, 6%, 7%, 8%, 9%, 10%, 20%, 30%, 40%, 50%, 60%, 70%, 80%, 90% or more in sinusoid formation or sinusoidal red blood cell volume in an osteonecrotic tissue (e.g., osteonecrotic bone), relative to the degree of sinusoid formation or sinusoidal red blood cell volume prior to the administering step, is indicative that vascular density is increased in the osteonecrotic tissue.

In some embodiments, the LLP2A peptidomimetic ligand-bisphosphonate drug conjugates as described herein are used for reducing or preventing cell death in an osteonecrotic tissue. In some embodiments, cell death in an osteonecrotic tissue is measured by detecting the presence of empty osteocytic lacunae in a bone. Thus, in some embodiments, the prevention of cell death or reduction in the rate of cell death in an osteonecrotic tissue (e.g., bone) from administration of a pharmaceutical composition as described herein (e.g., compositions comprising a conjugate of an LLP2A peptidomimetic ligand and a bisphosphonate drug (e.g., LLP2A-Ale)) can be measured by comparing the amount of empty osteocytic lacunae in an osteonecrotic tissue prior to and subsequent to administration of the pharmaceutical composition. In some embodiments, the empty lacunae are detected by imaging (e.g., MRI or radiography). In some embodiments, the empty lacunae are detected by histopathologic examination, e.g., of a bone biopsy sample from the subject. In some embodiments, a stabilization in the amount of empty lacunae in the osteonecrotic tissue prior to and subsequent to administration of the pharmaceutical composition (e.g., wherein the number of empty lacunae in the osteonecrotic tissue subsequent to administration of the pharmaceutical composition is substantially the same as the number of empty lacunae in the osteonecrotic tissue prior to administration of the pharmaceutical composition) is indicative of the prevention or reduction of cell death in the osteonecrotic tissue.

In some embodiments, a method of treating osteonecrosis as described herein further comprises increasing the rebuilding of bone (e.g., in conjunction with increasing vascular density and/or reducing cell death in the osteonecrotic bone or joint). In some embodiments, the method of treating osteonecrosis comprises increasing the number of osteoblasts present on the bone surface in areas where osteonecrosis is observed. Bone growth can be measured in a variety of ways known to one of skill in the art. Methods of measuring bone growth include, but are not limited to, micro CT, Dual X-ray absorption, ultrasound, QCT, SPA, DPA, DXR, SEXA, QUS, X-ray, or marker analysis such as Alizarin red S, serum osteocalcin, serum alkaline phosphatase, Serum bone Gla-protein (BGP), bone mineral content, serum calcium, serum phosphorus, tantalum markers, and serum IGF-1. In some embodiments, an increase of at least about 0.1%, 0.5%, 1%, 2%, 3%, 4%, 5%, 6%, 7%, 8%, 9%, 10%, 20%, 30%, 40%, 50%, 60%, 70%, 80%, 90% or more in bone density in an osteonecrotic tissue (e.g., osteonecrotic bone), relative to the bone density prior to the administering step, is indicative that bone rebuilding is increased in the osteonecrotic tissue.

V. EXAMPLES

The following examples are offered to illustrate, but not to limit, the claimed invention.

Example 1

Figure 1:
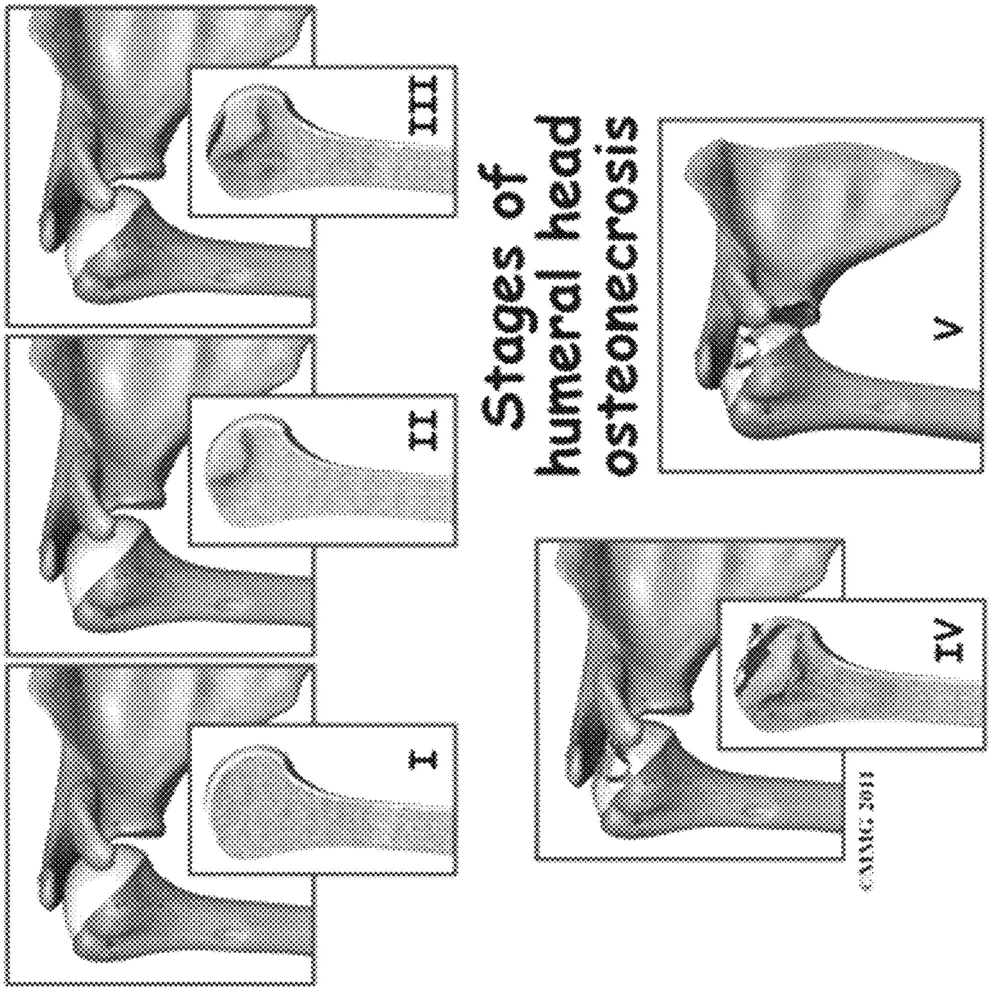
FIG. 1. Stages of osteonecrosis. Stages of osteonecrosis are depicted for humeral head osteonecrosis. Initially there is a reduction in blood supply, followed by death of bone cells, then collapse of the humerus because the area of dead bone cannot support the use of the joint.

Use of LLP2A-Ale in a 56 Day Mouse Model of Glucocorticoid-Induced Osteonecrosis Osteonecrosis is a disease that is characterized by reduced blood flow to bones, particular to bones in joints. The reduced blood supply results in the death and breakdown of the bone. FIG. 1 depicts the stages of glucocorticoid induced osteonecrosis. Osteonecrosis is classified in stages (I through V) referring to how far the disease has progressed. With atraumatic osteonecrosis, initially there is a reduction in blood supply, which results in the death of bone cells, then collapse of the bone (in FIG. 1, the humerus) because the area of dead bone cannot support the use of the bone.

Figure 2:
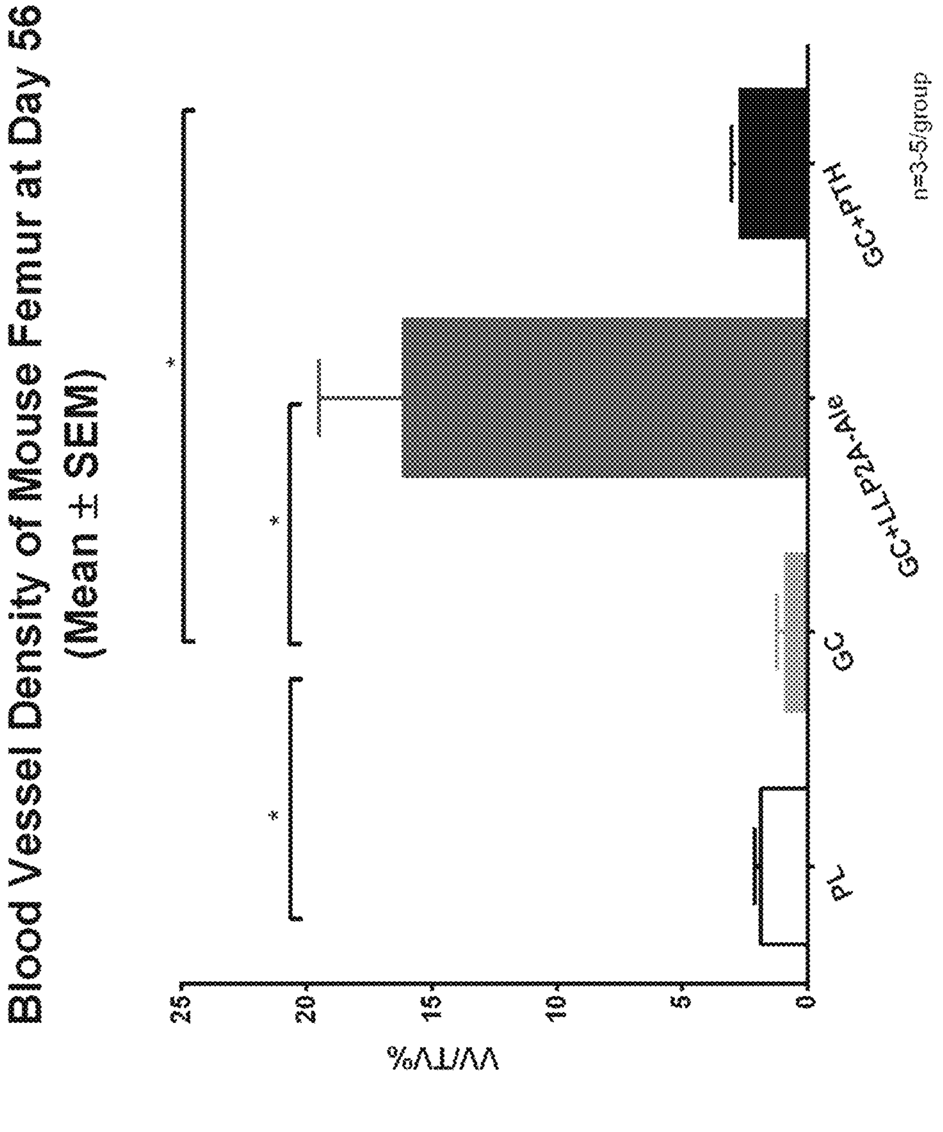
FIG. 2. Blood vessel density of femurs from glucocorticoid-treated mice. 4 month old male mice were treated glucocorticoid ("GC") or placebo for 56 days. At day 28 a group of glucocorticoid-treated mice were treated with LLP2A-Ale or PTH for an additional 28 days. Blood vessel density of the femur was measured after sacrifice by microCT according to published methods. * $p<0.05$ between GC and PL, GC+LLP2A-Ale was significantly different from all other groups, and GC+PTH was significantly different from all other groups.
Figure 3:
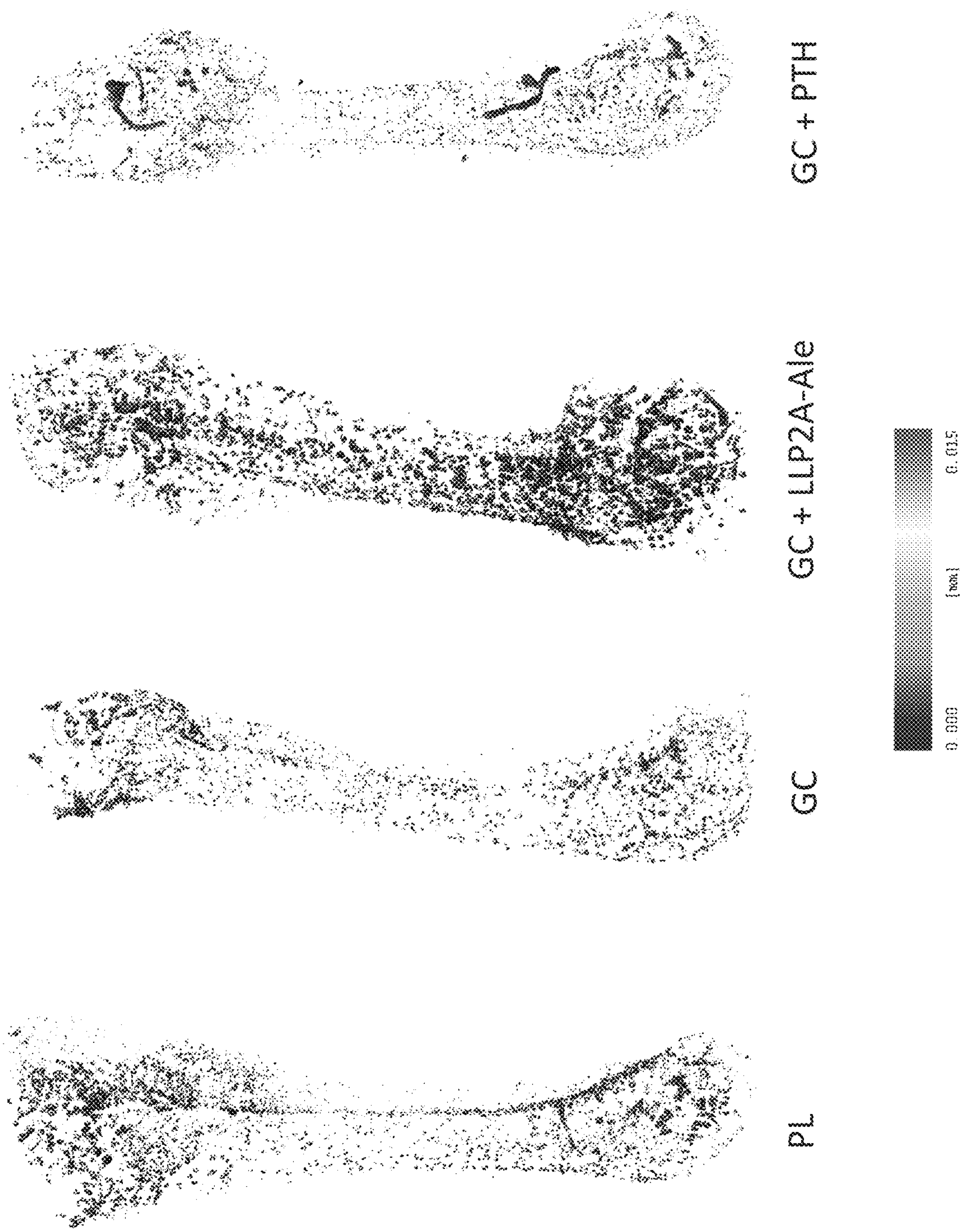
FIG. 3. Vascular density of femurs from glucocorticoid-treated mice. 4 month old male mice were treated with glucocorticoid or placebo for 56 days. At day 28 a group of glucocorticoid-treated mice were treated with LLP2A-Ale or PTH for an additional 28 days. At day 56 animals were given a contrast agent and then sacrificed and then the animals femurs were decalcified and then scanned by microCT. Compared to the placebo group, GC treatment reduced blood vessel density. GC+LLP2A-Ale increased vascular density compared to GC alone, and GC+PTH did not significantly change vascular density.

The efficacy of LLP2A-Ale was evaluated using a mouse model of glucocorticoid-induced osteonecrosis. 4-month-old male mice were treated for 56 days with glucocorticoids. At day 28, a group of mice was treated with either LLP2A-Ale or PTH for an additional 28 days. Blood vessel density of the femur was measured after sacrifice by microCT according to published methods. As shown in FIG. 2, the blood vessel density of the femurs of mice treated with glucocorticoid and LLP2A-Ale was significantly higher than the negative control (glucocorticoid-only treated) mice or mice treated with glucocorticoid and PTH. Vascular density of the femurs of glucocorticoid-treated mice subsequently treated with LLP2A-Ale or PTH was also assessed by giving the mice a contrast agent, then sacrificing the mice, decalcifying the femurs, and scanning the femurs by microCT. As shown in FIG. 3, glucocorticoid treatment reduced blood vessel density. Treatment of the glucocorticoid-treated mice with LLP2A-Ale increased vascular density compared to glucocorticoid alone, while the glucocorticoid-treated mice who were further treated with PTH did not exhibit a significant change in vascular density very much relative to glucocorticoid treatment alone. These data show that part of glucocorticoid-induced osteonecrosis is reduced vascularity, and LLP2A-Ale increases vascular density in the osteonecrotic tissue. Without being bound to a particular theory, it is believed that LLP2A-Ale promotes increased vascularity by bringing MSCs to the bone that is turning over with osteonecrosis, which stimulates new blood vessel formation, which in turn is needed to stimulate new bone formation in the osteonecrotic bone.

Figure 4:
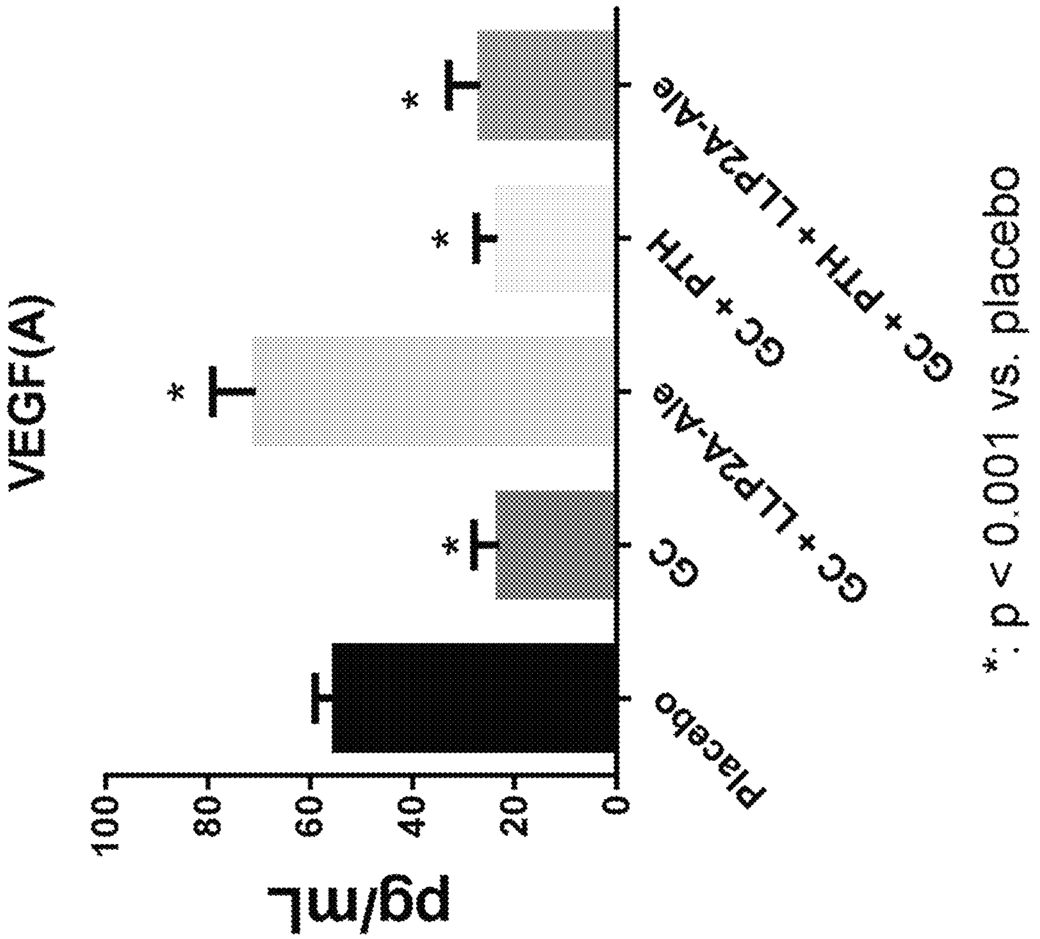
FIG. 4. Serum VEGF-A levels in glucocorticoid-treated mice. Mice treated with placebo (PL), glucocorticoid (GC), glucocorticoid and 250 μg/kg LLP2A-Ale (GC+LLP2A-Ale), glucocorticoid and PTH (GC+PTH), or glucocorticoid and PTH and 250 μg/kg LLP2A-Ale (GC+PTH+LLP2A-Ale) were measured for serum levels of VEGF. GC treatment reduced serum levels of VEGF, while GC+LLP2A-Ale returned the levels to placebo treated animals.

Increased blood vessel formation can also be assessed by marker analysis. For example, VEGF is a pro-angiogenic factor and stimulates new blood vessel formation. As shown in FIG. 4, VEGF serum levels were measured on day 56 from the animals in the treatment study that had glucocorticoid treatment alone from day 1-28, then either glucocorticoid or placebo alone, or glucocorticoid+LLP2A-Ale, or glucocorticoid+PTH, or glucocorticoid+PTH+LLP2A-Ale. PTH was given 20 ug/kg 5× a week, while LLP2A-Ale was given at 500 ug/kg at day 28 only. Glucocorticoid treatment reduced serum levels of VEGF as measured by ELISA in duplicate, while glucocorticoid+LLP2A-Ale returned the levels of serum VEGF to those of placebo treated animals.

Figure 5:
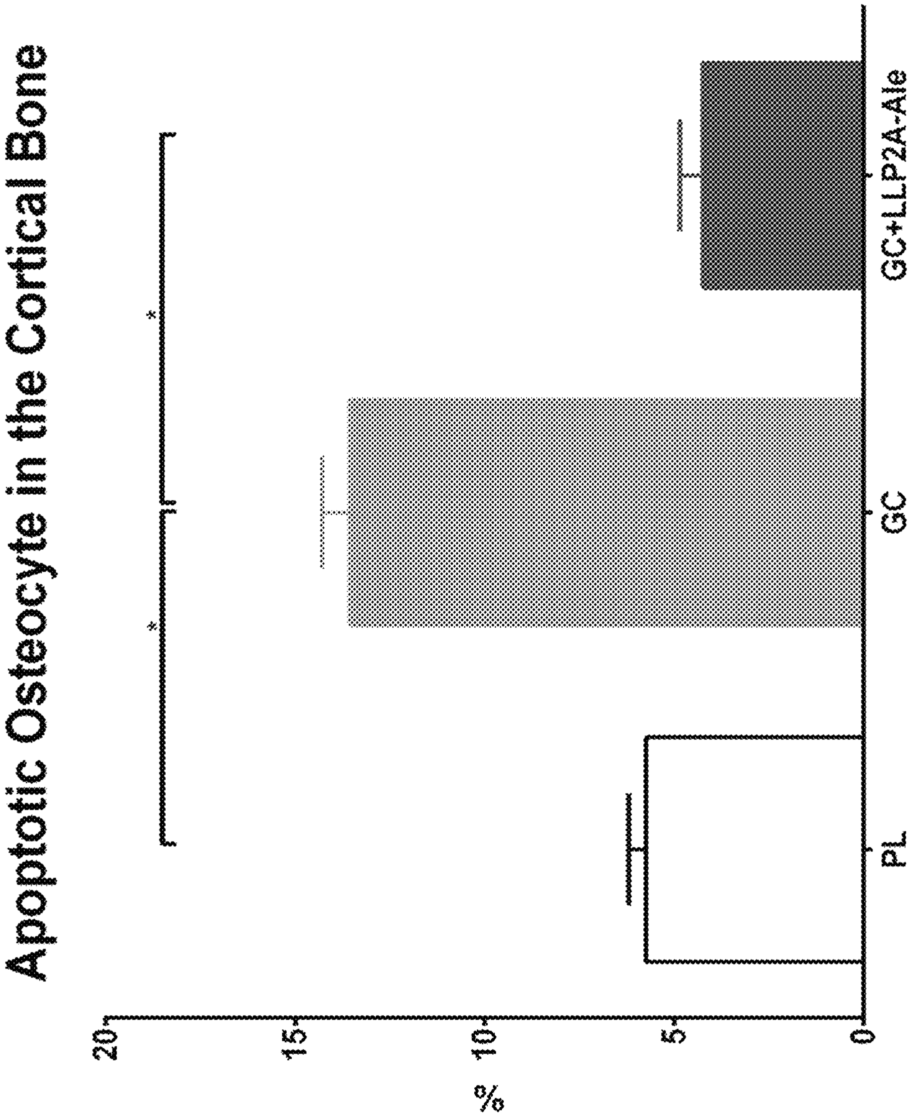
FIG. 5. Cortical bone osteocyte apoptosis. Mice were treated with PL for 56 days, GC alone for 56 days or GC alone for 28 days, then GC plus one dose of LLP2A-Ale at day 28. Animals were sacrificed at day 56 and the percent of osteocytes that were apoptotic were measured. GC treatment alone at day 56 increased the number of osteocytes that were apoptotic, and GC+LLP2A-Ale prevented osteocyte apoptosis. * $p<0.05$ from all other groups at day 28 study.

Osteocytes die from loss of blood supply and also from glucocorticoid treatment. As shown in FIG. 5, we counted apoptotic osteocytes from the cortical bone sections from the glucocorticoid treatment study described above, in which animals were treated with PL for 56 days, GC alone for 56 days or GC alone for 28 days, then GC+ one dose of LLP2A-Ale at day 28. The animals were sacrificed at day 56, the bones were decalcified and then TUNEL assays were performed to determine the number of apoptotic osteocytes. Glucocorticoid treatment alone, at day 56 increased the number of osteocytes that were apoptotic. Glucocorticoid+LLP2A-Ale treatment prevented osteocyte apoptosis. Since osteonecrosis has apoptotic osteocytes, this data suggests that LLP2A-Ale can treat osteonecrosis of the bone.

Figure 6:
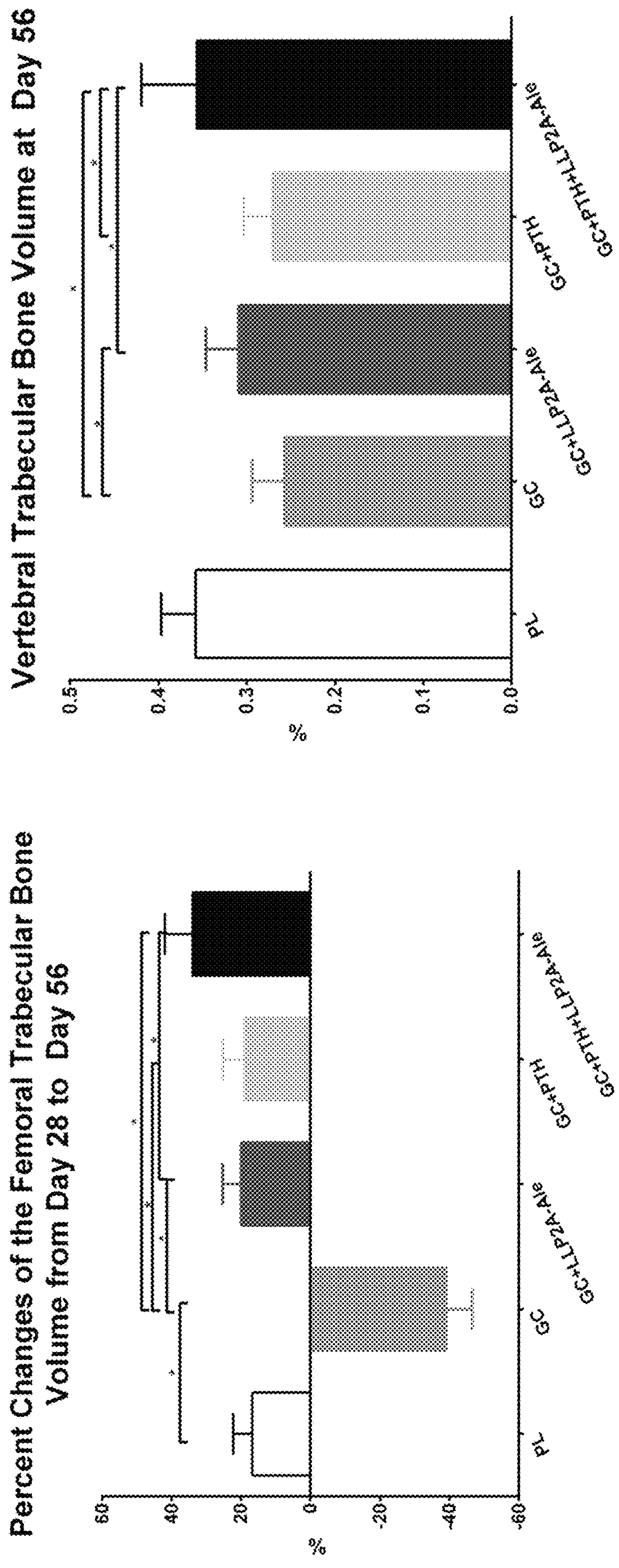
FIG. 6. Trabecular bone volume in glucocorticoid-treated mice. Mice were treated for 28 days with glucocorticoid (GC), then treated with either LLP2A-Ale, PTH, or LLP2A-Ale+PTH. The outcome measure was the change in trabecular bone mass from day 28 to 56, measured in vivo at the distal femur (left panel) and change in trabecular bone mass for the vertebral trabecular bone volume (right panel). Mice receiving GC treatment alone lost nearly 40% trabecular bone mass at the distal femur from day 28 to 56, while treatments with GCs and either LLP2A-Ale or PTH increased the trabecular bone volume to the baseline/sham level. The combination of GC+LLP2A-Ale+PTH increased the trabecular bone mass at the distal femur to greater than the placebo (PL) group. In the vertebrae, the combination of GC+LLP2A-Ale+PTH restored the trabecular bone mass to levels for the placebo (PL) group. *, $p<0.05$ from all other groups at day 56; #, $p<0.05$ vs. GC.

Treatment with LLP2A-Ale also rebuilds bone in a mouse model of glucocorticoid-induced osteonecrosis. As shown in FIG. 6, mice were treated for 28 days with glucocorticoids, then treated with either LLP2A-Ale, PTH, or LLP2A-Ale+PTH. Changes in trabecular bone mass during the treatment period for the distal femur and vertebral trabecular bone volume were measured. For both the distal femur and vertebrae, treatment with LLP2A-Ale increased the bone volume relative to the glucocorticoid-treated mice. For the distal femur trabecular bone volume, treatment with LLP2A-Ale increased the distal femur trabecular bone volume to the baseline/sham level.

Example 2

Use of LLP2A-Ale in a 90 Day Mouse Model of Glucocorticoid-Induced Osteonecrosis This study was conducted to determine whether LLP2A-Ale can reverse or treat established traumatic osteonecrosis in mice.

Materials and Methods

Animals and Experimental Procedures

The efficacy of LLP2A-Ale was evaluated over a 90 day study using a mouse model of glucocorticoid-induced osteonecrosis. Seven week-old male mice (BALB/c (n=80, Jackson laboratories, USA) were housed in a sanitary ventilated animal room maintained at 20° C. with a 12-hour light/dark cycle. All animals were handled according to the USDA animal care guidelines with the approval of the UC Davis Committee on Animal Research. The mice were given water and standard commercial rodent chow (22/5 Rodent Diet; Teklad, Madison, WI) ad libitum. The animals were weight randomized to either a placebo group (fresh water) or glucocorticoid only (4 mg/L dexamethasone (Dex) in drinking water) and treated for 90 days. At day 30, the Dex-treated mice were then re-randomized to Dex alone, Dex+250 μg/kg LLP2A-Ale, Dex+500 μg/kg LLP2A-Ale and Dex+750 μg/kg LLP2A-Ale. The LLP2A-Ale treatments were given on days 30, 45, 60 and 75. Additionally, 0.1 mg/kg methotrexate was administered twice weekly by subcutaneous injection from day 1-42 in all groups receiving glucocorticoid.

All the mice were euthanized at day 90. The body weights of all the study animals were assessed each week. If the study animals had 10% loss of body weight compared to the previous week, the dose of dexamethasone was reduced to 2 mg/L, until weight gain was observed. All of the animals were injected with calcein (30 mg/kg) and alizarin red (20 mg/kg) at 7 and 2 days before euthanization.

Histological Analysis

Both the right and left distal femurs were fixed in 10% neutral buffered formalin and were shaken for 3 days, then decalcified in 5% EDTA until the bones were fully decalcified. The specimens were then processed in ascending concentrations of ethanol and embedded in paraffin. Tissue sections were cut into 5 microns sections, stained with hematoxylin and eosin and evaluated for the presence of osteonecrosis by bright field microscopy at 20× magnification. Experimental methods are also described in Mohan et al., *Calif Tissue Int* (2016) doi:10.1007/s00223-016-0195-6, which is incorporated herein by reference in its entirety for all purposes. Osteonecrosis was detected using modified criteria reported by Yang el al., (a mouse model for glucocorticoid-induced osteonecrosis: Effect of a steroid holiday. J Orthop Res. 2009; 27:169-75) which defines osteonecrosis as requiring all of the following changes: (1) empty lacunae, (2) pyknotic osteocyte nuclei in areas of empty lacunae and necrosis of adjacent bone marrow, (3) presence of excessive fat cells in the bone marrow, (4) cartilage degradation and (5) presence of fibrin thrombi in the blood vessels. In addition, trabecular bone volume, adipose volume, sinusoid volume and osteoblast surface at the distal femoral epiphyses were measured. Empty lacunae density was calculated by empty lacunae/total osteocytes within the entire distal femoral epiphysis region for each sample. Each section was scored by two experienced histologists, then a consensus reading was performed by two additional experienced histologists.

Results

Body Weight

The body weight of BALB/c mice in the placebo group had an increase in weight over the experimental period of 90 days that was significantly different from the baseline weight ($p<0.05$) but this was not observed in the other groups. The body weight of all dexamethasone (Dex) treated animals was significantly lower compared to placebo from day 7 up to day 90 ($p<0.05$).

Prevalence of Osteonecrosis

Figure 7:
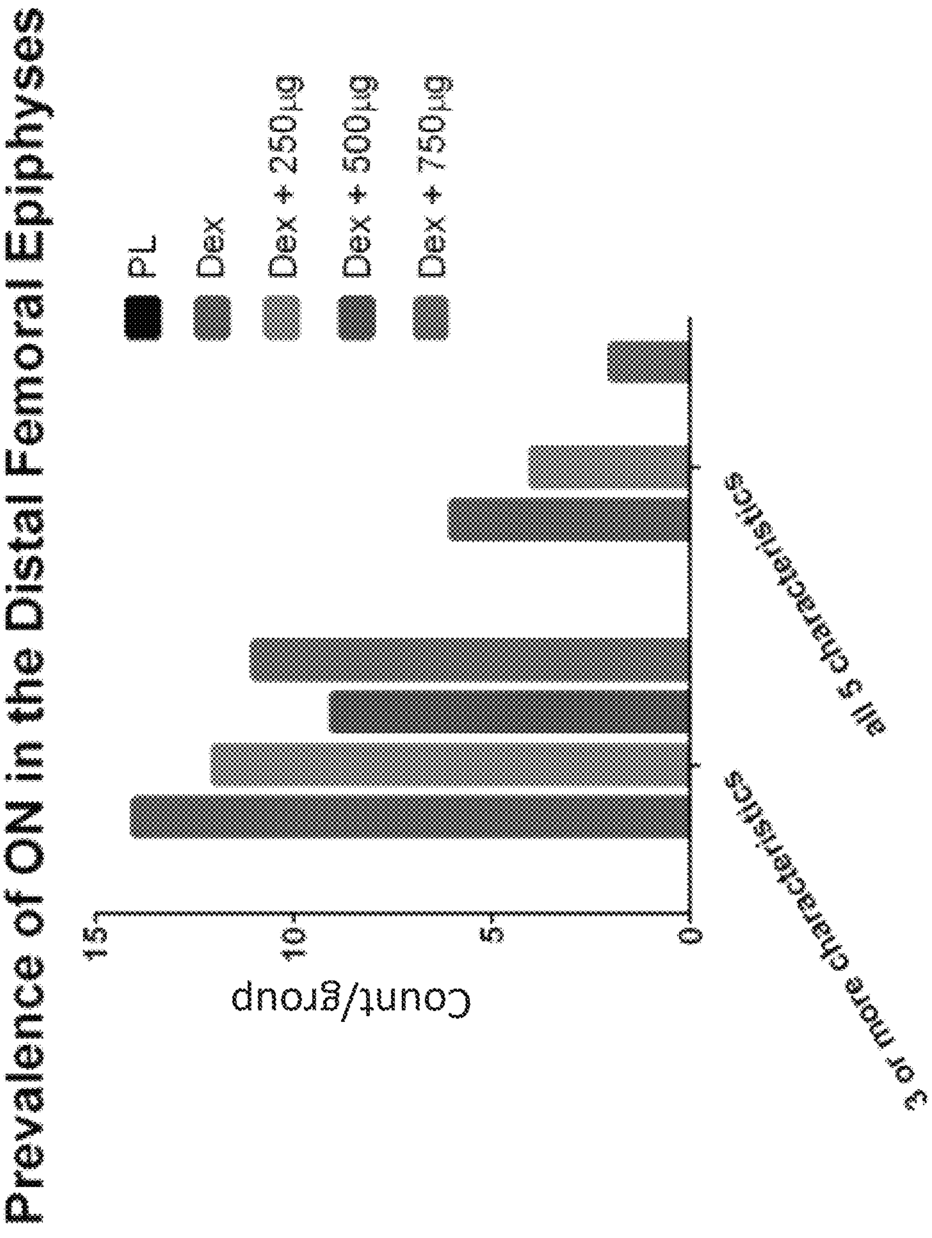
FIG. 7. Prevalence of osteonecrosis in dexamethasone-treated mice. Mice were treated for 90 days with dexamethasone (Dex), 4 mg/l in drinking water or placebo (PL) (fresh water). At day 30, the Dex-treated mice were re-randomized to Dex alone, Dex+250 μg/kg LLP2A-Ale, Dex+500 μg/kg LLP2A-Ale, and Dex+750 μg/kg LLP2A-Ale. The LLP2A-Ale treatments were given on days 30, 45, 60, and 75. All mice were euthanized at day 90. Right and left distal femurs were fixed in 10% neutral buffer formalin and decalcified. The specimens were dehydrated, embedded in paraffin, cut into 5 micron sections and H&E stained. The sections were evaluated for osteonecrosis by bright light microscopy using modified criteria reported by Yang et al., J. Orthop. Res., 27:169-75 (2009)), which defines osteonecrosis by the presence of the five following characteristics: (1) empty lacunae, (2) pyknotic osteocyte nuclei in areas of empty lacunae and necrosis of adjacent bone marrow, (3) presence of excessive fat cells in the bone marrow, (4) cartilage degradation, and (5) presence of fibrin thrombi in the blood vessels. Each GC-treated group and placebo group were assessed for all five osteonecrosis characteristics or the presence of at least three of the five osteonecrosis characteristics described above. Fewer mice receiving LLP2A-Ale treatments exhibited three or more osteonecrosis characteristics as compared to mice treated with Dex alone (Dex only group: 14/16 (88%); Dex+LLP2A-Ale 250 μg/kg: 12/16 (75%); Dex+LLP2A-Ale 500 μg/kg: 9/16 (56%); and LLP2A-Ale 750 μg/kg: 11/16 (69%). The number of mice per treatment group demonstrating all five osteonecrosis characteristics also decreased in mice receiving LLP2A-Ale treatment as compared to treatment with Dex alone.
Figure 8A:
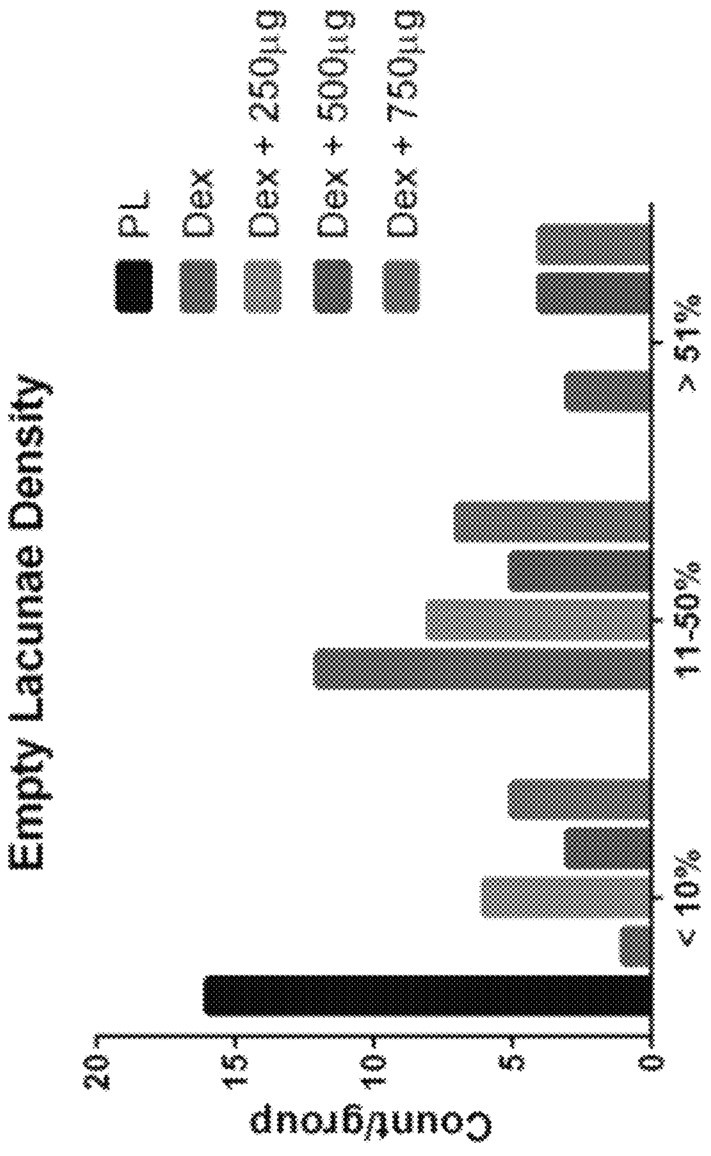
FIG. 8A-8B. Empty lacunae density of femurs from in dexamethasone-treated mice. Mice treated with placebo (PL), dexamethasone alone (Dex), Dex+250 μg/kg LLP2A-
Figure 8B:
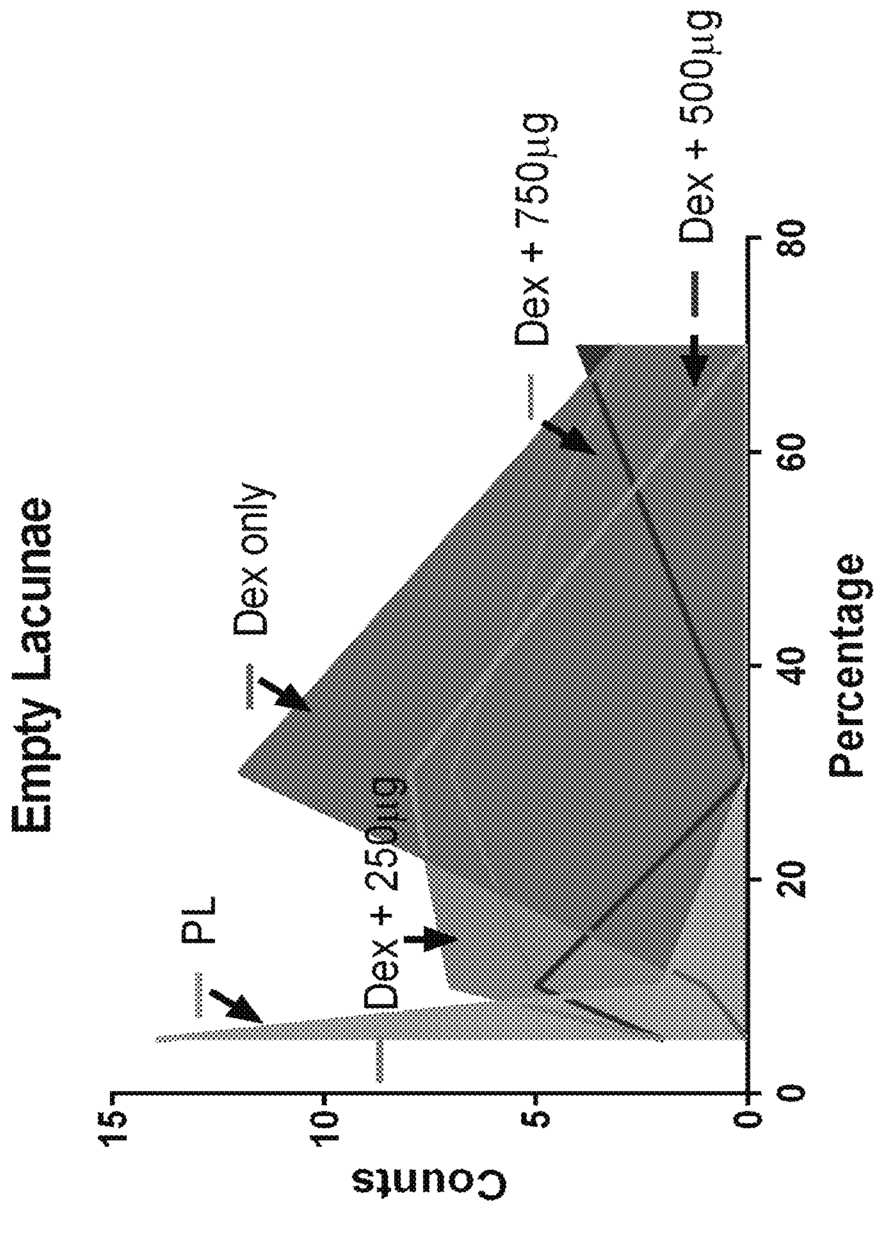

Evidence of osteonecrosis was present throughout the epiphyses of the distal femurs in Dex-treated mice. As shown in FIG. 7, the Dex alone treatment group showing at least three, or all five osteonecrosis characteristics (as determined using the modified criteria reported by Yang el al) was significantly higher than the number of subjects in any of the Dex+LLP2A-Ale treatment groups. For samples that have three or more characteristics for osteonecrosis: PL (0%); Dex only group 14/16 (88%); Dex+LLP2A-Ale 250 μg/kg 12/16 (75%); Dex+LLP2A-Ale 500 μg/kg 9/16 (56%) and LLP2A-Ale 750 μg/kg 11/16 (69%). In the Dex only group, 75% of the samples had 10% or more empty lacunae (FIG. 8A-B) as compared to 44-62% of the samples in LLP2A-Ale-treated groups. Also as shown in FIG. 8A-B, more samples in the LLP2A-Ale treatment groups exhibited less than 10% empty lacunae as compared to the Dex-treated group.

Histological Evaluations of Dexamethasone Treated-Mice

As shown in FIGS. 9A and 9B, histological sections of epiphyses from placebo treated mice showed no evidence of osteonecrosis lesions with a few marrow fat cells and sinusoids being observed in the bone marrow. The histological sections of the epiphyses from the Dex treated mice (FIG. 9C-9F) showed necrotic trabeculae characterized by large empty lacunae (FIGS. 9D and 9F, black arrows), and nuclear pyknosis of osteocytes. Some dexamethasone-treated mice displayed loss of the articular cartilage (FIG. 9D, yellow arrows), surrounded by necrotic bone marrow (FIG. 9E, green arrows) and fat tissue (FIGS. 9D, 9E, and 9F, blue arrows). These data show that glucocorticoid-induced osteonecrosis is observed in this mouse model over a 90 day study.

Repair of Osteonecrotic Lesions in LLP2A-Ale Treated Mice

As shown in FIG. 10A, all three dosages of LLP2A-Ale treatment reduced adipose volume as compared to the adipose volume of Dex-treated mice, demonstrating evidence of repair of the osteonecrosis lesions. As shown in FIG. 10B, all three dosages of LLP2A-Ale treatment increased sinusoid volume as compared to placebo or Dex-alone treatment. Increasing the LLP2A-Ale treatment above 250 μg/kg led to a marginal decrease in sinusoid volume. These data suggests that LLP2A-Ale treatment can repair osteonecrotic lesions by increasing vascularization.

Histological Evaluations of LLP2A-Ale Treated-Mice

Figure 11A:
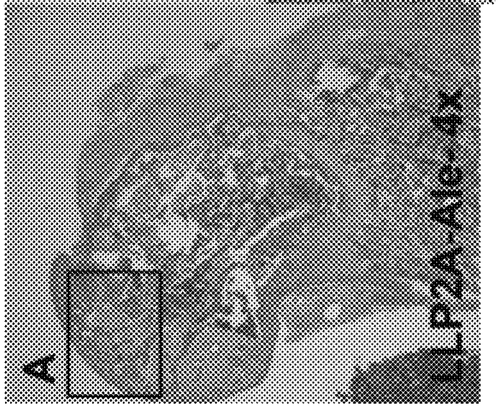
Figure 11B:
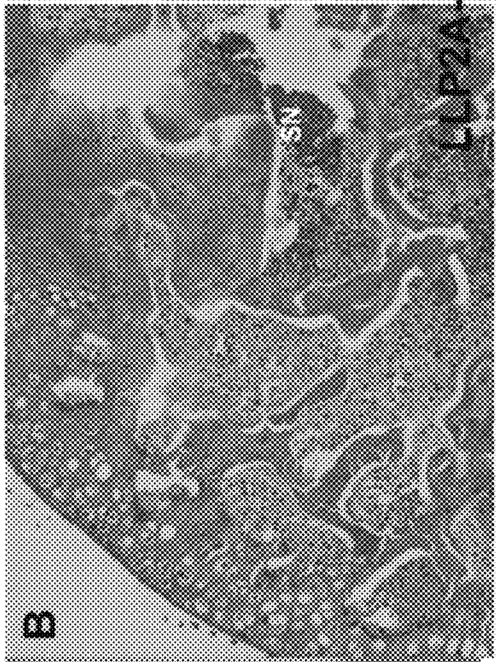
Figure 11C:
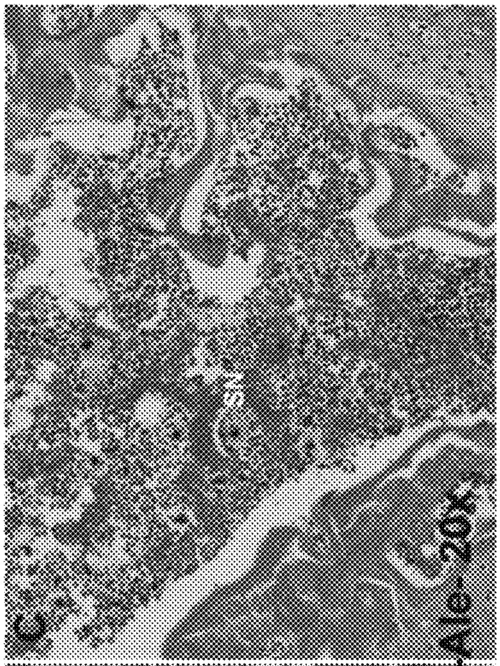
Figure 11D:
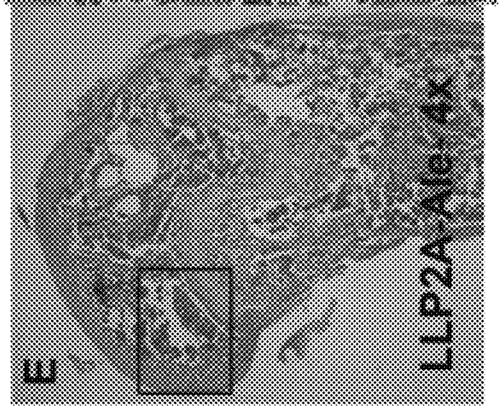
Figure 11E:
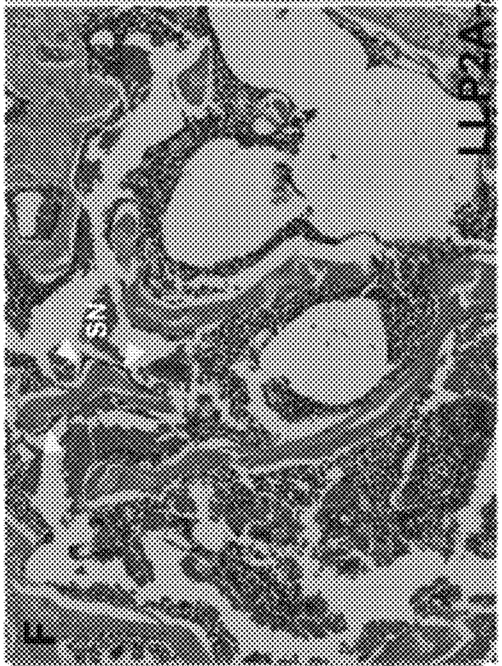
Figure 11F:
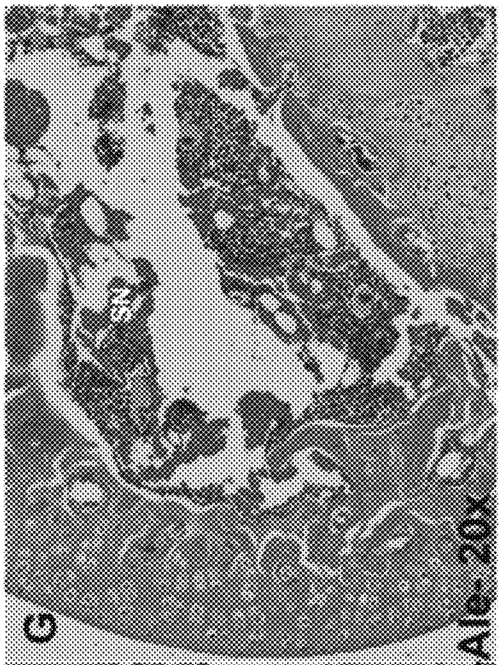

As shown in FIGS. 11A through 11F, histological sections of epiphyses from LLP2A-Ale treated mice showed increased sinusoid formation, projecting into necrotic bone marrow (FIG. 11B) or occupied in bone marrow where there was no bone marrow necrosis being observed (FIGS. 11E & 11F). In FIG. 11E, some osteoblasts were observed at the trabecular bone surface and close to the sinusoids (yellow arrow). These data suggest that LLP2A-Ale treatment after osteonecrosis was observed appeared to reduce the number of empty lacunae/pyknotic nuclei, adipocyte density in the bone marrow and increased the sinusoidal red blood cell volume, and maintained the cellularity of the bone marrow compared to dexamethasone alone. In addition, LLP2A-Ale treatment appeared to reduce the amount of fibrin within the bone marrow, and increased the number of osteoblasts present on the bone surface in areas of the epiphyses where osteonecrosis was present, suggesting an ability to stimulate new bone formation.

Example 3

Use of LLP2A-Ale and hPTH (1-34) to Prevent Glucocorticoid-Induced Osteonecrosis and Reduction in Vascularity in a Mouse Model This study was conducted to determine whether administration of LLP2A-Ale or hPTH (1-34) over a 30-day or 45-day period can prevent glucocorticoid-induced osteonecrosis and maintain the vasculature within the distal femur in mice.

Materials and Methods

Animals and Experimental Procedures

The efficacy of LLP2A-Ale and hPTH (1-34) was evaluated over a 30 and 45 day study using a mouse model of glucocorticoid-induced osteonecrosis. Seven week-old male BALB/c mice were randomized into Placebo group (fresh water), glucocorticoid only (4 mg/L dexamethasone (Dex) in drinking water), Dex+250 μg/kg LLP2A-Ale, Dex+500 μg/kg LLP2A-Ale, or Dex+40 μg/kg hPTH (administered five times a week) for 30 or 45 days. At day 30 or 45, the mice were sacrificed. Study endpoints included histological evidence of osteonecrosis, bone mass, and prevalent blood vessels (CD31 and Endomucin expression) in the distal femur, and was performed as set forth in Example 2. Non-parametric Kruskal-Wallis tests were used to determine the differences between the groups.

Results

Prevalence of Osteonecrosis

Evidence of osteonecrosis was present throughout the epiphyses of the distal femurs in Dex-treated mice. As shown in FIG. 12, the Dex alone treatment group had a significantly higher percentage of osteonecrosis prevalence than mice in the LLP2A-Ale or hPTH treatment groups. The incidence of glucocorticoid-induced osteonecrosis was 57% on day 30 and 73% on day 45 for Dex alone, and both LLP2A-Ale and hPTH (1-34) treatment prevented incident GC-induced osteonecrosis lesions.

Histological Evaluations

Histological sections of the epiphyses from the Dex-treated mice showed significantly reduced trabecular bone volume and trabecular thickness compared to placebo on day 30 and 45 ($p<0.05$). Trabecular number was significantly reduced on day 45 ($p<0.05$). In contrast, both LLP2A-Ale and hPTH (1-34) treated animals had higher bone volume and lower trabecular separation compared to the Dex group on day 30 and 45 ($p<0.05$). Additionally, as compared to LLP2A-Ale, hPTH (1-34), or placebo treatment, Dex treatment decreased the staining intensity of both CD31 and Endomucin expression on day 30 and 45 (data not shown). These data show that glucocorticoid-induced osteonecrosis is observed in this mouse model over a 30 and 45 day study.

CONCLUSION

Dex treatment induced trabecular bone loss and osteonecrosis lesions. Both LLP2A-Ale and hPTH treatment reduced the incidence and severity of osteonecrosis and maintained the vascular integrity of the distal femur.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating osteonecrosis in a subject classified as having Stage 2, 3, or 4 disease by the Ficat classification system, the method comprising:

(a) detecting in the subject at least one osteonecrotic lesion having a size of more than 5 $cm^2$ in at least one bone; wherein the osteonecrosis is traumatic osteonecrosis or glucocorticoid-induced osteonecrosis or alcohol-induced osteonecrosis, and (b) administering locally to the subject a pharmaceutical composition comprising a conjugate of LLP2A and Alendronate ("LLP2A-Ale") having the formula:

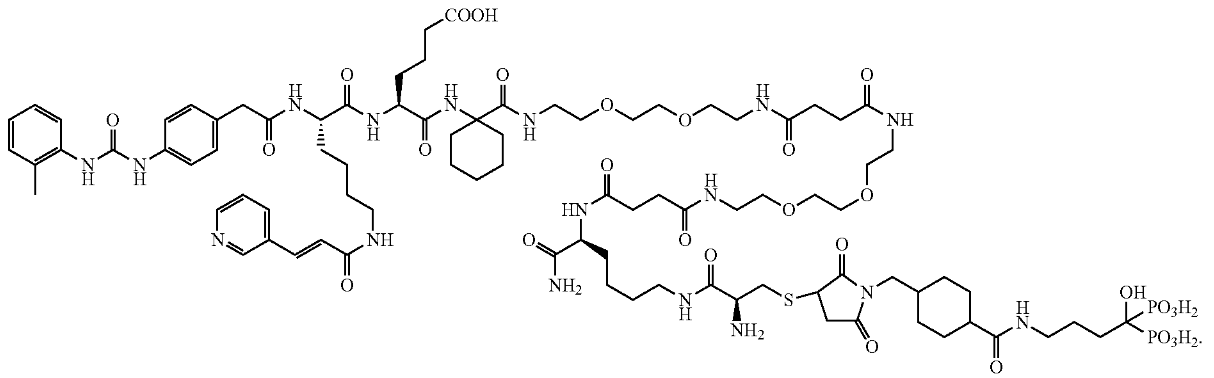

2. The method of claim 1, wherein the method further comprises administering exogenous mesenchymal stem cells.

3. The method of claim 2, wherein the pharmaceutical composition and the exogenous mesenchymal stem cells are administered concurrently.

4. The method of claim 2, wherein the pharmaceutical composition and the exogenous mesenchymal stem cells are administered sequentially.

5. The method of claim 1, wherein the pharmaceutical composition is administered locally at the site of the at least one osteonecrotic lesion.

6. A method of increasing vascular density in an osteonecrotic tissue in a subject classified as having Stage 2, 3, or 4 disease by the Ficat classification system, the method comprising:

(a) detecting in the subject at least one osteonecrotic lesion having a size of more than 5 $cm^2$ in at least one bone, wherein the osteonecrosis is traumatic osteonecrosis or glucocorticoid-induced osteonecrosis or alcohol-induced osteonecrosis, and (b) administering locally to the subject a pharmaceutical composition comprising a conjugate of LLP2A and Alendronate ("LLP2A-Ale") having the formula:

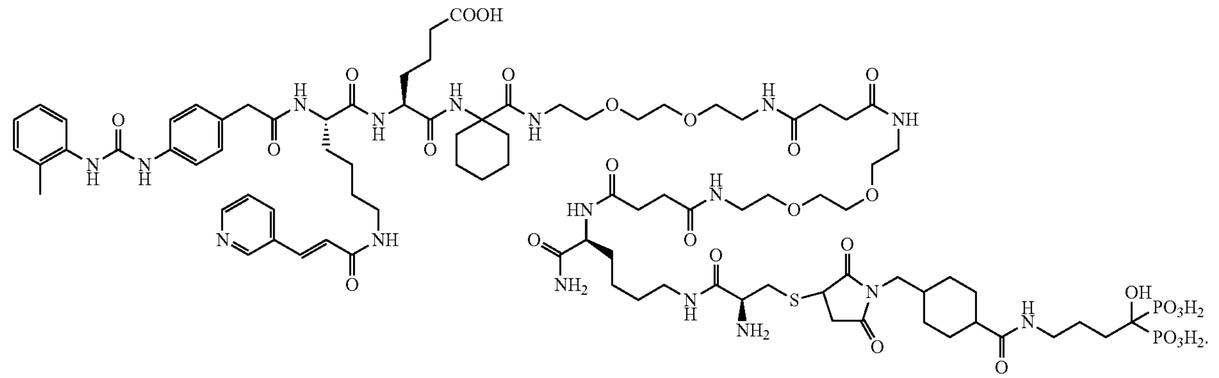

7. The method of claim 6, wherein the method further comprises administering exogenous mesenchymal stem cells.

8. A method of preventing or reducing cell death in an osteonecrotic tissue in a subject classified as having Stage 2, 3, or 4 disease by the Ficat classification system, the method comprising:

(a) detecting in the subject at least one osteonecrotic lesion having a size of more than 5 $cm^2$ in at least one bone; wherein the osteonecrosis is traumatic osteonecrosis or glucocorticoid-induced osteonecrosis or alcohol-induced osteonecrosis; and (b) administering locally to the subject a pharmaceutical composition comprising a conjugate of LLP2A and Alendronate ("LLP2A-Ale") having the formula:

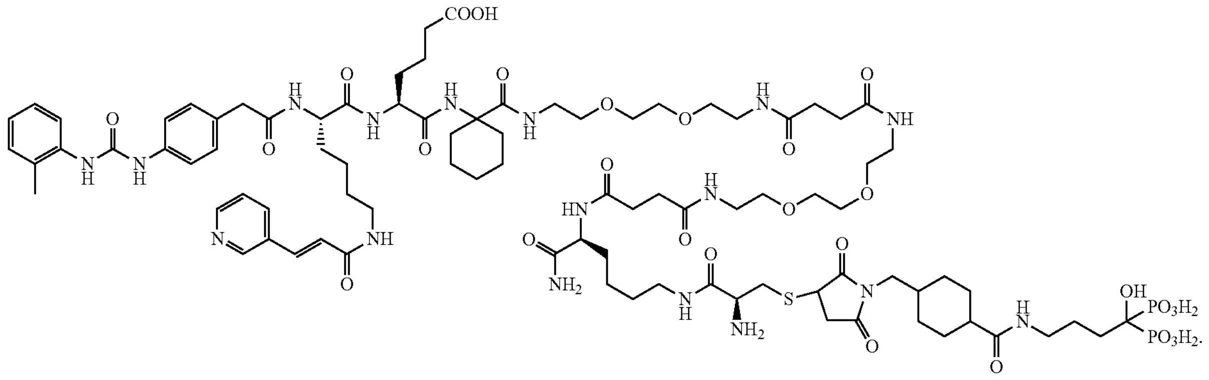

9. The method of claim 8, wherein the method further comprises administering exogenous mesenchymal stem cells.

10. The method of claim 1, wherein the osteonecrosis is traumatic osteonecrosis.

11. The method of claim 1, wherein the method further comprises administering an anabolic agent to the subject.

12. The method of claim 11, wherein the anabolic agent is a parathyroid hormone (PTH) or an analog thereof.

13. The method of claim 11, wherein the anabolic agent is PTH 1-34 (teriparatide).

* * * * *